(12) United States Patent
Liao et al.

(10) Patent No.: US 11,773,043 B2
(45) Date of Patent: Oct. 3, 2023

(54) SYSTEMS AND METHODS FOR PRODUCING COENZYME Q10

(71) Applicants: INNER MONGOLIA KINGDOMWAY PHARMACEUTICAL CO., LTD., Inner Mongolia (CN); XIAMEN KINGDOMWAY GROUP COMPANY, Fujian (CN)

(72) Inventors: Weicheng Liao, Hohhot (CN); Bingrong Wang, Hohhot (CN); Dan Li, Hohhot (CN); Luming Xu, Hohhot (CN); Sifu Jiang, Hohhot (CN)

(73) Assignees: INNER MONGOLIA KINGDOMWAY PHARMACEUTICAL CO., LTD., Hohhot (CN); XIAMEN KINGDOMWAY GROUP COMPANY, Xiamen (CN)

( * ) Notice: Subject to any disclaimer, the term of this patent is extended or adjusted under 35 U.S.C. 154(b) by 207 days.

(21) Appl. No.: 16/690,305

(22) Filed: Nov. 21, 2019

(65) Prior Publication Data
US 2020/0087235 A1   Mar. 19, 2020

Related U.S. Application Data

(63) Continuation of application No. PCT/CN2018/098991, filed on Aug. 6, 2018.

(51) Int. Cl.
C07C 46/10 (2006.01)
G01N 30/02 (2006.01)
(Continued)

(52) U.S. Cl.
CPC .............. *C07C 46/10* (2013.01); *G01N 30/02* (2013.01); *G01N 2030/027* (2013.01); *G01N 2030/065* (2013.01); *G01N 2030/085* (2013.01)

(58) Field of Classification Search
None
See application file for complete search history.

(56) References Cited

U.S. PATENT DOCUMENTS

| 9,440,901 B2 | 9/2016 | Kawachi et al. |
| 2004/0197886 A1 | 10/2004 | Ueda et al. |

(Continued)

FOREIGN PATENT DOCUMENTS

| CN | 101445435 A | 6/2009 |
| CN | 101314597 B | 12/2010 |

(Continued)

OTHER PUBLICATIONS

Ning Yan-Li, et al., Structure Identification of Coenzyme Q10 and It's Impurities, Journal of Instrumental Analysis, 11 (27): 266-269, 2008.

(Continued)

*Primary Examiner* — Kara M Peo
(74) *Attorney, Agent, or Firm* — METIS IP LLC

(57) ABSTRACT

A system and method for purifying coenzyme $Q_{10}$ are provided. The method includes: passing a $CoQ_{10}$-containing crude product through a first chromatographic column to obtain a first $CoQ_{10}$-containing intermediate product. The method further includes preparing, based on the first $CoQ_{10}$-containing intermediate product, a second $CoQ_{10}$-containing intermediate product. The method further includes passing the second $CoQ_{10}$-containing intermediate product through a second chromatographic column to obtain a third $CoQ_{10}$-containing intermediate product. The method further (Continued)

includes obtaining purified $CoQ_{10}$ product by purifying the third $CoQ_{10}$-containing intermediate product.

9 Claims, 6 Drawing Sheets

(51) Int. Cl.
*G01N 30/06* (2006.01)
*G01N 30/08* (2006.01)

(56) References Cited

U.S. PATENT DOCUMENTS

| | | |
|---|---|---|
| 2010/0004473 A1 | 1/2010 | Kanaya et al. |
| 2011/0137084 A1 | 6/2011 | Berl et al. |
| 2017/0209812 A1* | 7/2017 | Dlugasch ............. G01N 30/463 |

FOREIGN PATENT DOCUMENTS

| | | |
|---|---|---|
| CN | 101987815 A | 3/2011 |
| CN | 102391092 B | 5/2013 |
| CN | 104402697 B | 5/2016 |
| CN | 103819326 B | 8/2016 |
| CN | 107337593 A | 11/2017 |
| CN | 107445615 A | 12/2017 |
| CN | 108218681 A | 6/2018 |
| CN | 108795968 A | 11/2018 |

OTHER PUBLICATIONS

International Search Report in PCT/CN2018/098991 dated May 6, 2019, 4 pages.
Written Opinion in PCT/CN2018/098991 dated May 6, 2019, 4 pages.

* cited by examiner

SYSTEMS AND METHODS FOR PRODUCING COENZYME Q10

CROSS-REFERENCE TO RELATED APPLICATIONS

This application is a continuation of International Application No. PCT/CN2018/098991, filed on Aug. 6, 2018, which designates the United States of America, the contents of which are incorporated herein by reference in their entirety.

TECHNICAL FIELD

The present disclosure generally relates to methods for producing coenzyme $Q_{10}$ ($CoQ_{10}$), and in particular, to methods for isolating and purifying $CoQ_{10}$ from $CoQ_{10}$-containing crude product.

BACKGROUND

Coenzyme $Q_{10}$ ($CoQ_{10}$) is a lipid-soluble quinone homolog. It mainly presents in mitochondria, lysosome, Golgi body, microsome, cell membrane and the like. $CoQ_{10}$ is a substance indispensable to the functional maintenance of the body. It is known to be involved in the activation of adenosine triphosphate (ATP) production as a constituent component of the electron transport system in mitochondria, antioxidant action in the body and membrane stabilization. $CoQ_{10}$ has been used for food, pharmaceutical agent, cosmetic, or the like. Also, $CoQ_{10}$ is one of the important members of the mitochondrial respiratory chain.

$CoQ_{10}$ can be obtained according to conventionally-known methods such as extraction from animal and/or plant tissues, chemical synthesis, and microbial fermentation. When $CoQ_{10}$ is produced by the aforementioned methods, various impurities are contained therein including, for example, coenzyme $Q_9$, coenzyme $Q_{10}$ isomeride, coenzyme $Q_{11}$. Certain purification methods such as crystallization have been employed to purify $CoQ_{10}$, but these methods may have various deficiencies, such as the low yield of $CoQ_{10}$, high impurity content, large amount of using solvent, high energy consumption. It may, therefore, be desirable to provide systems and methods for purifying coenzyme $Q_{10}$ with higher yield, lower production cost, and better efficiency for removing impurities.

SUMMARY

According to an aspect of the present disclosure, a method for producing purified coenzyme $Q_{10}$ ($CoQ_{10}$) is provided. The method may include one or more following operations: passing a $CoQ_{10}$-containing crude product through a first chromatographic column to obtain a first $CoQ_{10}$-containing intermediate product; preparing, based on the first $CoQ_{10}$-containing intermediate product, a second $CoQ_{10}$-containing intermediate product; passing the second $CoQ_{10}$-containing intermediate product through a second chromatographic column to obtain a third $CoQ_{10}$-containing intermediate product; obtaining purified $CoQ_{10}$ product by purifying the third $CoQ_{10}$-containing intermediate product.

In some embodiments, a purity of the purified $CoQ_{10}$ product is equal to or greater than 99.7%.

In some embodiments, the first chromatographic column is a normal-phase chromatographic column, and the second chromatographic column is a reverse-phase chromatographic column.

In some embodiments, the first chromatographic column is a reverse-phase chromatographic column, and the second chromatographic column is a normal-phase chromatographic column.

In some embodiments, the passing a $CoQ_{10}$-containing crude product through a first chromatographic column to obtain a first $CoQ_{10}$-containing intermediate product may include: loading the $CoQ_{10}$-containing crude product into the first chromatographic column; eluting the first chromatographic column with a first eluent; collecting a first $CoQ_{10}$-containing eluate from the first chromatographic column to obtain the first $CoQ_{10}$-containing intermediate product.

In some embodiments, the first eluent of the first chromatography may be a normal-phase eluent.

In some embodiments, the first eluent of the first chromatography may be a reverse-phase eluent.

In some embodiments, the second eluent of the second chromatography may be a normal-phase eluent.

In some embodiments, the second eluent of the second chromatography may be a reverse-phase eluent.

In some embodiments, the normal-phase eluent may include a first solvent and a second solvent. The first solvent may include at least one of n-hexane, 2-methylbutane, cyclopentane, 2-methylpentane, 2,2-dimethylbutane, 2,3-dimethylbutane, methylcyclopentane, cyclohexane, n-heptane, 2-methylhexane, 3-methylhexane, 2,3-dimethylpentane, 2,4-dimethylpentane, methylcyclohexane, octane, 2,2,3-trimethylpentane, isooctane, ethylcyclohexane, or 1-octene. The second solvent includes at least one of isopropyl ether, acetone, ethyl acetate, butanone, dichloromethane, methyl acetate, propyl acetate, isopropyl acetate, butyl acetate, methyl propionate, ethyl propionate, butyl propionate, diethyl ether, methanol, ethanol, n-propanol, isopropanol, n-butanol, isobutanol, or acetonitrile. The at least one of the second solvent may be 2-10% of the normal-phase eluent by volume.

In some embodiments, the reverse-phase eluent may include a fourth solvent and a fifth solvent. The fourth solvent may include at least one of acetone, ethyl acetate, butanone, dichloromethane, methyl acetate, propyl acetate, isopropyl acetate, butyl acetate, methyl propionate, ethyl propionate, butyl propionate, diethyl ether, isopropyl ether, n-propanol, isopropanol, n-butanol, or isobutanol. The fifth solvent may include at least one of alcohol, methanol, acetonitrile, or water. The fourth solvent may have a ratio of 20-60% among the reverse-phase eluent.

In some embodiments, the passing the second $CoQ_{10}$-containing intermediate product through a second chromatographic column to obtain a third $CoQ_{10}$-containing intermediate product may include: dissolving the second $CoQ_{10}$-containing intermediate product with a third solvent; loading the dissolved second $CoQ_{10}$-containing intermediate product into the second chromatographic column; eluting the second chromatographic column with a second eluent; collecting a second $CoQ_{10}$-containing eluate from the second chromatographic column; concentrating the second $CoQ_{10}$-containing eluate to obtain the third $CoQ_{10}$-containing intermediate product.

In some embodiments, the third solvent may include at least one of acetone, ethyl acetate, butanone, dichloromethane, methyl acetate, propyl acetate, isopropyl acetate, butyl acetate, methyl propionate, ethyl propionate, butyl propionate, diethyl ether, isopropyl ether, n-propanol, isopropanol, n-butanol, or isobutanol; and at least one of alcohol, methanol, acetonitrile, or water. The at least one of acetone, ethyl acetate, butanone, dichloromethane, methyl acetate, propyl acetate, isopropyl acetate, butyl acetate, methyl propionate, ethyl propionate, butyl propionate, diethyl ether, isopropyl ether, n-propanol, isopropanol, n-butanol, or isobutanol is 40-90% of the third solvent by volume.

In some embodiments, a pressure of the first chromatographic column or a pressure of the second chromatographic column ranges from 3 to 300 bar.

In some embodiments, the purifying the third $CoQ_{10}$-containing intermediate product to obtain the purified $CoQ_{10}$ product may include crystallizing the third $CoQ_{10}$-containing intermediate product.

In some embodiments, the crystallization of the third $CoQ_{10}$-containing intermediate product includes vacuum crystallization with adiabatic cooling.

In some embodiments, the crystallization of the third $CoQ_{10}$-containing intermediate product includes solvent-out crystallization.

In some embodiments, the crystallization of the third $CoQ_{10}$-containing intermediate product includes an ultrasound crystallization.

In some embodiments, the crystallization of the third $CoQ_{10}$-containing intermediate product includes a continuous crystallization.

In some embodiments, the method may further include one or more following operations: obtaining a mother liquor from the crystallization of the third $CoQ_{10}$-containing intermediate product; separating $CoQ_{10}$ from the mother liquor.

In some embodiments, the separating $CoQ_{10}$ from the mother liquor may include: obtaining a fourth $CoQ_{10}$-containing intermediate product by passing the mother liquor through at least one chromatographic column; obtaining $CoQ_{10}$ by purifying the fourth $CoQ_{10}$-containing intermediate product through at least one crystallization.

In some embodiments, the at least one chromatographic column includes a normal-phase chromatographic column or a reverse-phase chromatographic column.

In some embodiments, the at least one crystallization includes at least one of vacuum insulation crystallization, solvent-out crystallization, ultrasound crystallization, or continuous crystallization.

In some embodiments, the separating $CoQ_{10}$ from the mother liquor may include: concentrating the mother liquor to obtain a mother liquor concentrate; dissolving the mother liquor concentrate with a sixth solvent; loading the sixth solvent containing the mother liquor concentrate to a third chromatographic column; eluting the third chromatographic column with a third eluent; collecting a third $CoQ_{10}$-containing eluate from the third chromatographic column; concentrating the third $CoQ_{10}$-containing eluate; crystallizing the concentrated third $CoQ_{10}$-containing eluate to obtain the purified $CoQ_{10}$.

BRIEF DESCRIPTION OF THE DRAWINGS

The present disclosure is further described in terms of exemplary embodiments. The foregoing and other aspects of embodiments of present disclosure are made more evident in the following detail description when read in conjunction with the attached drawing figures, and wherein.

DETAILED DESCRIPTION

Figure 1:
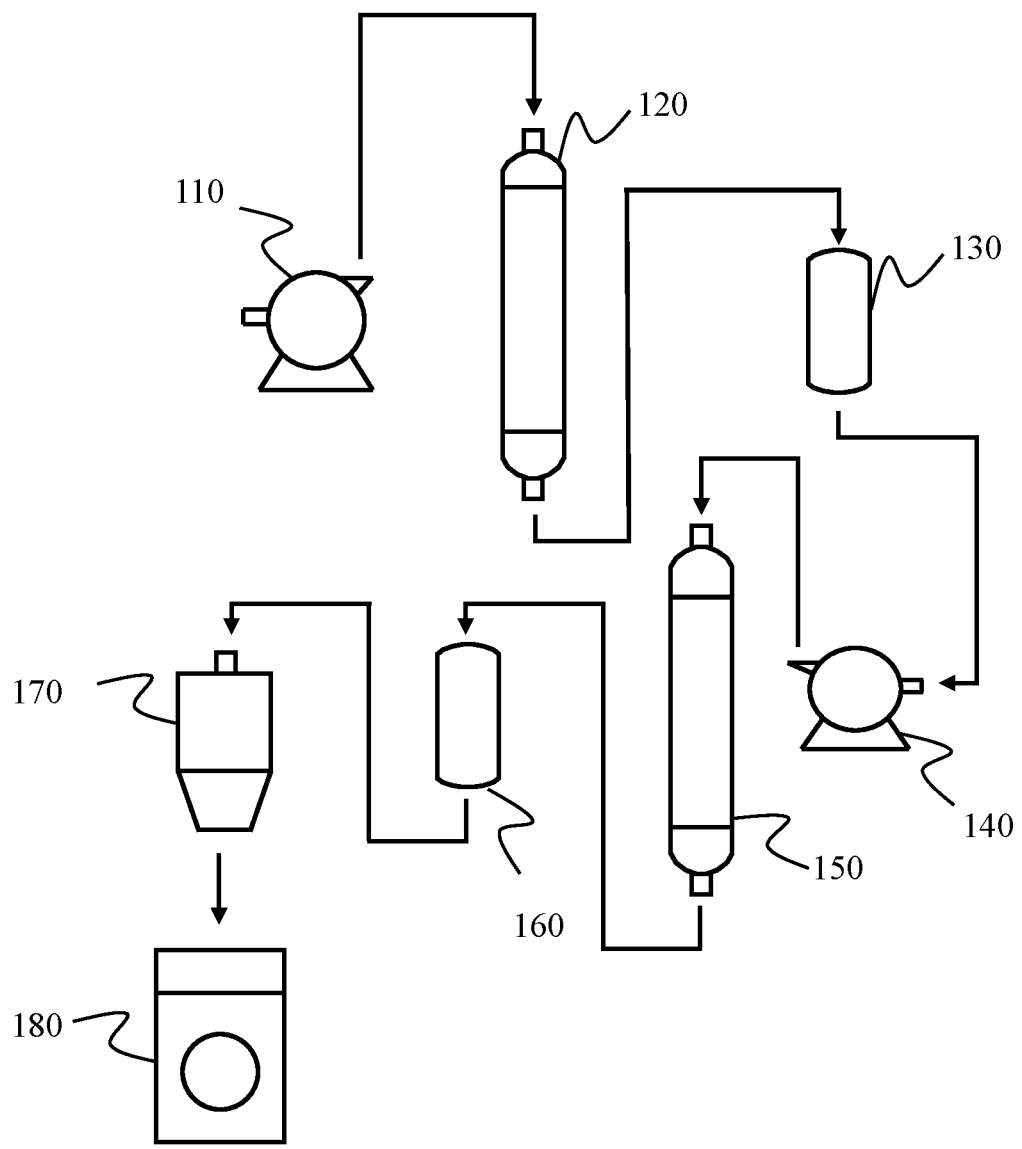
FIG. 1 is a schematic diagram illustrating an exemplary system 100 for purifying $CoQ_{10}$ according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure.

It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order or simultaneously. Moreover, one or more other operations may be added to the flowcharts. One or more operations may be removed from the flowcharts.

FIG. 1 is a schematic diagram of a system 100 for purifying coenzyme $Q_{10}$ ($CoQ_{10}$) according to some embodiments of the present disclosure. The system 100 may be a chemical purification equipment for purifying chemical industry materials and/or products. The system 100 may include one or more pumps (e.g., pump 110 and pump 140), one or more chromatographic columns (e.g., chromatographic column 120 and chromatographic column 150), one or more concentrators (e.g., concentrator 130 and concentrator 160), a crystallizer 170, and a dryer 180.

The pump 110 may be configured to transfer a $CoQ_{10}$-containing crude product as loading sample to the chromatographic column 120. In some embodiments, the $CoQ_{10}$-containing crude product may be obtained by various methods, for example, an animal and/or plant tissue extraction method, a chemical synthesis method, a microbial fermentation method, or the like. In some embodiments, the pump 110 may include a gear pump, a centrifugal pump, a screw pump, a reciprocation pump, a pneumatic diaphragm pump, a peripheral pump, a mix flow pump, an axial flow pump, a steam-jet pump, a self-priming pump, a piston pump, a booster pump, or the like, or a combination thereof. The pump 110 may transfer the $CoQ_{10}$-containing crude product at a flow rate, which may depend on the capacity of the chromatographic column 120.

The chromatographic column 120 (which is also referred to herein as the first chromatographic column) may be configured to elute the $CoQ_{10}$-containing crude product to obtain a primary $CoQ_{10}$ purification product. The $CoQ_{10}$-containing crude product may be loaded to and pass through the chromatographic column 120, and the first chromatographic column may be eluted by a first eluent. The primary $CoQ_{10}$ purification product (which is also referred to herein as a first $CoQ_{10}$-containing intermediate product) may be the eluate coming out of the chromatographic column 120, which may contain all or part of the $CoQ_{10}$ in the $CoQ_{10}$-containing crude product received by the chromatographic column 120.

In some embodiments, the first eluent may include petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a combination thereof. The first eluent may include hydrocarbons, fatty acid esters, nitriles, ethers, ketones, alcohols, fatty acids, or the like, or a solution thereof, or any mixture thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not be limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination thereof. Exemplary aromatic hydrocarbon may include but not be limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not be limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane or the like, or a solution thereof, or a combination thereof. In some embodiments, the fatty acid may include but not be limited to propionic acid ester, acetic acid ester, formic acid ester, or the like, or a solution thereof, or a combination thereof. Exemplary propionic acid ester may include but not be limited to methyl propionate, ethyl propionate, butyl propionate and isopentyl propionate, or the like, or a solution thereof, or a combination thereof. Exemplary acetic acid ester may include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not be limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not be limited to acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not be limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not be limited to acetone, methylethylketone, methyl butyl ketone, methyl isobutyl ketone, or the like, or a solution thereof, or a combination thereof. In some embodiments, the alcohol may be cyclic or non-cyclic. The alcohol may be saturated or unsaturated. Exemplary alcohol may include but be not limited to monovalent alcohol, divalent alcohol, trivalent alcohol, or the like, or a solution thereof, or a combination thereof. The monovalent alcohol may include but not be limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not be limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. Preferably, the first eluent may include but not be limited to petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a solution thereof, or a combination thereof.

In some embodiments, the chromatographic column 120 may be a normal-phase chromatographic column or a reverse-phase chromatographic column. In some embodiments, the stationary phase of a normal-phase chromatographic column may be silica gel, alumina, or a bonded phase filler having a polar functional group, or the like. The bonded phase filler may be a silica gel-based filler. The polar functional group may be bonded to the surface of the silica gel of the silica gel-based filler. In some embodiments, the polar functional group may include an amido group, a cyano group, a diol group, or the like, or a combination thereof.

In some embodiments, the stationary phase of the reverse-phase chromatographic column may be a bonded phase filler having a weak polarity functional group. The bonded phase filler may be a silica gel-based filler, and the weak polarity functional group may be bonded to the surface of the silica gel of the silica gel-based filler. In some embodiments, the weak polarity functional group may include an octadecyl group, an octyl group, a butyl group, a trimethyl group, a phenyl group, or the like, or a combination thereof.

The concentrator 130 may be configured to remove the solvent from the eluate (i.e., the primary $CoQ_{10}$ purification product received from the chromatographic column 120) to obtain a $CoQ_{10}$-containing concentrate (which is also referred to herein as a second $CoQ_{10}$-containing intermediate product). In some embodiments, a commercially available concentrator or the like may be used. For example, the concentrator 130 may include a single-effect concentrator, a double-effect concentrator, a spherical concentrator, a vacuum concentrator, an evaporator, or the like, or a combination thereof. The evaporator may include but not limited to a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof.

The pump 140 may be configured to transfer the $CoQ_{10}$-containing concentrate (i.e., the second $CoQ_{10}$-containing intermediate product) to the chromatographic column 150 (which is also referred to herein as the second chromatographic column). The pump 140 may include a gear pump, a centrifugal pump, a screw pump, a reciprocation pump, a pneumatic diaphragm pump, a peripheral pump, a mix flow pump, an axial flow pump, a steam-jet pump, a self-priming pump, a piston pump, a booster pump, or the like, or a combination thereof.

The chromatographic column 150 may be configured to elute the $CoQ_{10}$-containing concentrate to obtain a secondary $CoQ_{10}$ purification product (which is also referred to herein as a third $CoQ_{10}$-containing intermediate product). The $CoQ_{10}$-containing concentrate may be loaded to and pass through the chromatographic column 150, and the secondary $CoQ_{10}$ purification product may accordingly be obtained. The secondary $CoQ_{10}$ purification product may be an eluate that includes $CoQ_{10}$ received from the chromatographic column 150. The eluent may include petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a combination thereof.

In some embodiments, the chromatographic column 150 may be a normal-phase chromatographic column or a reverse-phase chromatographic column. In some embodiments, the chromatographic column 150 and the chromatographic column 120 may be the same type of chromatographic column. For example, both the chromatographic column 120 and the chromatographic column 150 may be normal-phase chromatographic columns or reverse-phase chromatographic columns. Alternatively, the chromatographic column 120 and the chromatographic column 150 may be different types of chromatographic columns. For example, the chromatographic column 120 may be a normal-phase chromatographic column, and the chromatographic column 150 may be a reverse-phase chromatographic column; or the chromatographic column 120 may be a reverse-phase chromatographic column, and the chromatographic column 150 may be a normal-phase chromatographic column. In some embodiments, the stationary phase of a normal-phase chromatographic column may include silica gel, alumina, or a bonded phase filler having a polar functional group, or the like. The bonded phase filler may be a silica gel-based filler. The polar functional group may be bonded to the surface of the silica gel of the silica gel-based filler. In some embodiments, the polar functional group may include an amino group, a cyano group, a diol group, or the like, or a combination thereof.

In some embodiments, the stationary phase of the reverse-phase chromatographic column may include a bonded phase filler having a weak polarity functional group. The bonded phase filler may be a silica gel-based filler, and the weak polarity functional group may be bonded to the surface of the silica gel of the silica gel-based filler. In some embodiments, the weak polarity functional group may include an octadecyl group, an octyl group, a butyl group, a trimethyl group, a phenyl group, or the like, or a combination thereof.

The concentrator 160 may be configured to remove (or reduce) the solvent from the eluate (i.e., the secondary $CoQ_{10}$ purification product, which is also referred to herein as a third $CoQ_{10}$-containing intermediate product) to obtain a $CoQ_{10}$-containing concentrate. In some embodiments, a commercially available concentrator or the like may be used. For example, the concentrator 160 may include a single-effect concentrator, a double-effect concentrator, a spherical concentrator, a vacuum concentrator, an vaporator, or the like, or a combination thereof. The evaporator may include but not limited to a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof.

The crystallizer 170 may be configured to crystallize the secondary $CoQ_{10}$ purification product (i.e., the third $CoQ_{10}$-containing intermediate product) received from the chromatographic column 150 to obtain purified $CoQ_{10}$ crystal. For example, the crystallizer 170 may crystallize the secondary $CoQ_{10}$ purification product by using the cooling crystallization process. In some embodiments, the crystallizer 170 may include a cooling crystallizer, a Howard crystallizer, a stirred type crystallizer, a tower crystallizer, a double-pipe chiller, a rocker-type crystallizer, a drum crystallizer, a tank crystallizer, a vacuum crystallizer, a rotary crystallizer, a continuous operation circulation crystallizer, or the like, or a combination thereof. In some embodiments, one or more crystallization solvents may be used in the crystallization process. Exemplary crystallization solvents may include petroleum ether, methanol, alcohol, ethyl acetate, acetone, dichloromethane, trichloroethane, n-hexane, diethyl ether, isopropyl ether, isopropanol, acetonitrile, water, or the like, or a combination thereof.

In some embodiments, before the crystallization process, at least part of the eluent included in the secondary $CoQ_{10}$ purification product (i.e., the third $CoQ_{10}$-containing intermediate product) may be removed by an evaporation process, after which the processed secondary $CoQ_{10}$ purification product may undergo the crystallization process as described above.

In some embodiments, a centrifuge (not shown in FIG. 1) may be used to separate the $CoQ_{10}$ crystals from the crystallization solvent(s) after the crystallization process. For example, the centrifuge may be configured separate the $CoQ_{10}$ crystals from the crystallization solvent(s) by spinning at a high speed, and the $CoQ_{10}$ crystals may be retrieved from the centrifuge. In some embodiments, the centrifuge may be a vertical centrifuge, a horizontal centrifuge, a disk centrifuge, a gravity discharge screen centrifuge, a disk type centrifuge, a variable speed screen centrifuge, a peeler centrifuge, a sedimentation centrifuge, a batch centrifuge, a continuous centrifuge, manual unloading centrifuge, an automatic discharge centrifuge, a gyratory centrifuge, a vibrating centrifuge, a top suspended centrifuge, a piston push centrifuge, a tubular bowl centrifuge, a Groth type centrifuge, a multichamber centrifuge, a filtration type centrifuge, a decanter solid-bowl centrifuge, a constant speed screen centrifuge, a decanter solid-bowl centrifuge, a constant speed screen centrifuge, a vertical decanter centrifuge, a vibratory screen centrifuge, a ultra-high speed centrifuge, a decanter-disk combination centrifuge, a vertical worm screencen-trifuge, a screw peeler discharge screen centrifuge, an automatic continuous type screw discharge of solid centrifuge, a counter-current gas centrifuge with internal circulation, a multistep pusher centrifuge, a double step pasher centrifuge, a cylindrical-conical pusher centrifuge, a or the like, or a combination thereof.

The dryer 180 may be configured to dry or dehydrate the $CoQ_{10}$ crystal. For example, the dryer 180 may receive the $CoQ_{10}$ crystals and evaporate the crystallization solvent(s) included in the $CoQ_{10}$ crystals by, for example, heating up the $CoQ_{10}$ crystal. In some embodiments, one or more additional techniques may be utilized to facilitate the drying process, such as vacuuming the dryer 180, rolling or shaking the $CoQ_{10}$ crystals by the dryer 180, or a combination thereof, during the drying process. In some embodiments, the dryer 180 may include an extrusion dryer, an infrared dryer, a drum dryer, an ebullated dryer, a tunnel dryer, a spiral dryer, a kneading dryer, a vacuum dryer, a deep-bed dryer, a vertical disk dryer, a cylindrical dryer, a flash dryer, a cross current dryer, a parallel-flow dryer, a microwave dryer, a continuous dryer, a pneumatic dryer, a spray dryer, a nozzle jet dryer, a spin flash dryer, a fluidized bed dryer, a horizontal multi-compartment fluidized bed dryer, an adiabatic hot gas dryer, or the like, or a combination thereof.

In some embodiments, one or more components of the system 100 may be removed without affecting the implementation of the methods described in the present disclosure. For example, the concentrator 130 (and/or concentrator 160), the pump 140, and/or the chromatographic column 150 may be omitted from the system 100. The secondary $CoQ_{10}$ purification product (i.e., the third $CoQ_{10}$-containing intermediate product) obtained from the chromatographic column 120 may be directly transferred to the crystallizer 170 for crystallization. In some embodiments, two or more components of the system 100 may be combined into one component that has the functions of these components. For example, the centrifuge and the dryer 180 may be combined into one equipment that may both separate the $CoQ_{10}$ crystals from the crystallization solvent(s) and dry the $CoQ_{10}$ crystal.

Figure 2:
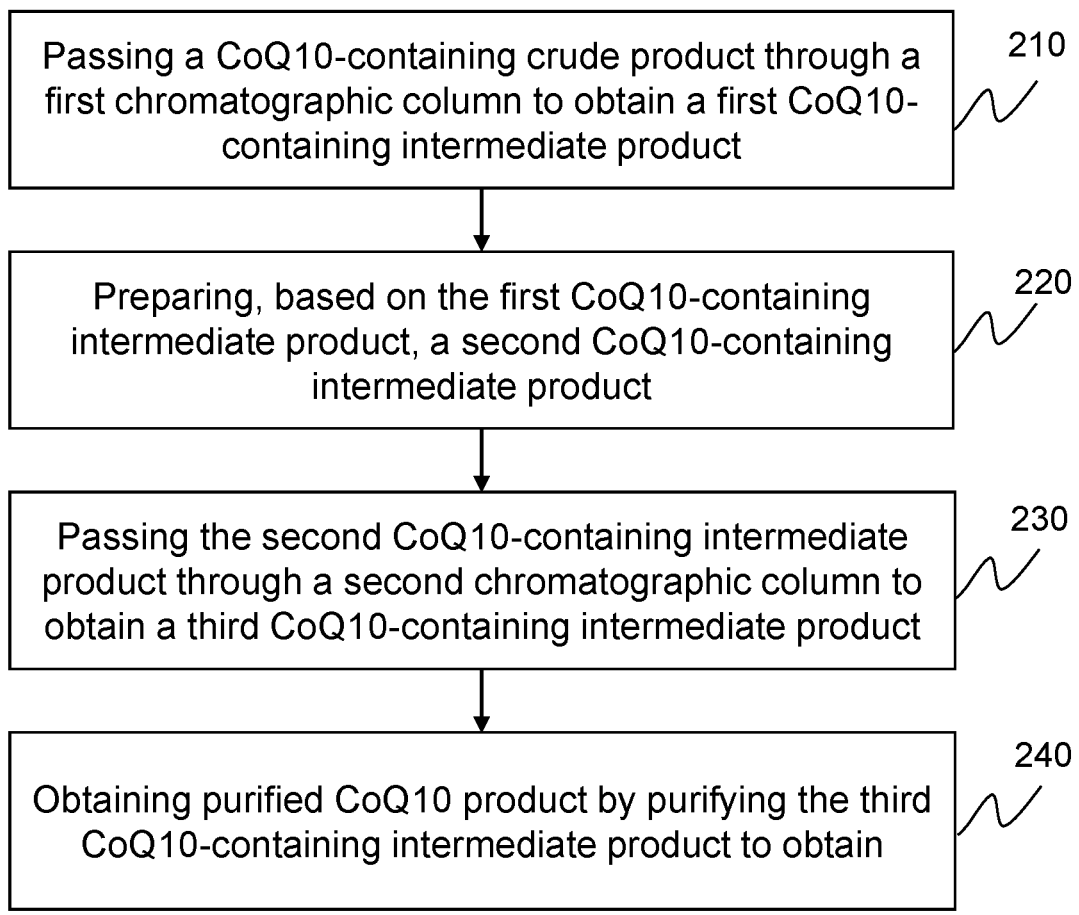
FIG. 2 is a flowchart of an exemplary process for obtaining purified $CoQ_{10}$ according to some embodiments of the present disclosure.

FIG. 2 is a flowchart of an exemplary process for obtaining purified $CoQ_{10}$ according to some embodiments of the present disclosure. In some embodiments, one or more steps in the process may be implemented based on the system 100 illustrated in FIG. 1.

In 210, a primary $CoQ_{10}$ purification product (also referred to herein as a first $CoQ_{10}$-containing intermediate product) may be obtained by passing a $CoQ_{10}$-containing crude product through a first chromatographic column (e.g., a chromatographic column 120). For example, a $CoQ_{10}$-containing crude product may be loaded into the first chromatographic column by a pump or a conveyor, for example, the pump 110, which may pass through the first chromatographic column.

The primary $CoQ_{10}$ purification product may be obtained. The $CoQ_{10}$-containing crude product may be a product including $CoQ_{10}$ and other impurity, for example, coenzyme $Q_9$, coenzyme $Q_{10}$ isomeride, and/or coenzyme $Q_{11}$. In some embodiments, the $CoQ_{10}$-containing crude product may be obtained by extracting from animal liver, animal myocardium, plant leaf, and/or plant seed. Alternatively or additionally, the $CoQ_{10}$-containing crude product may be obtained by chemical synthesis. Alternatively or additionally, the $CoQ_{10}$-containing crude product may be obtained by microbial fermentation.

The first chromatographic column may be a normal-phase chromatographic column or a reverse-phase chromatographic column. The $CoQ_{10}$-containing crude product may be loaded to the first chromatographic column, and the first chromatographic column may be eluted by a first eluent. The primary $CoQ_{10}$ purification product may be the eluate coming out of the first chromatographic column, which may contain all or part of the $CoQ_{10}$ in the $CoQ_{10}$-containing crude product received by the chromatographic column 120.

The first eluent to be used to elute the first chromatographic column may include hydrocarbons, fatty acid esters, nitriles, ethers, ketones, alcohols, fatty acids, or the like, or a solution thereof, or a combination thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination thereof. Exemplary aromatic hydrocarbon may include but not limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, diphenylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethaneor the like, or a solution thereof, or a combination thereof. In some embodiments, the fatty acid may include but not limited to propionic acid ester, acetic acid ester, formic acid ester, or the like, or a solution thereof, or a combination thereof. Exemplary propionic acid ester may include but not limited to methyl propionate, ethyl propionate, butyl propionate and isopentyl propionate, or the like, or a solution thereof, or a combination thereof. Exemplary acetic acid ester may include but not limited to methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not limited toacetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoicacid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not limited to acetone, methylethylketone, methylbutylketone, methylisobutylketone, or the like, or a solution thereof, or a combination thereof. In some embodiments, the alcohol may be cyclic or non-cyclic. The alcohol may be saturated or unsaturated. Exemplary alcohol may include but not limited to monovalent alcohol, divalent alcohol, trivalent alcohol, or the like, or a solution thereof, or a combination thereof. The monovalent alcohol may include but not limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. In some embodiments, the first eluent may be a normal-phase eluent including but not limited topetroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a solution thereof, or a combination thereof.

In some embodiments, the presence of $CoQ_{10}$ in the first eluate may be monitored according to a qualitative analysis method. Exemplary qualitative analysis method for monitoring the presence of $CoQ_{10}$ in the first eluate may include mass spectroscopy (MS), nuclear magnetic resonance (NMR) spectroscopy, infrared (IR) spectroscopy, ultraviolet-visible (UV/Vis) spectroscopy, gas chromatography (GC), liquid chromatography (LC), high performance liquid chromatography (HPLC), thin-layer chromatography (TLC), liquid chromatography-mass spectroscopy (LC-MS), or the like, or a combination thereof. Alternatively or additionally, the content of the $CoQ_{10}$ contained in the first eluate may be measured based on a quantitative analysis method. Exemplary quantitative analysis method for measuring the content of the $CoQ_{10}$ may include the GC, liquid chromatography, HPLC, spectrometer analysis method, or the like, or a combination thereof. The first eluate containing $CoQ_{10}$ may be collected if the first eluate contains the $CoQ_{10}$. The collected first eluate may be designated as the first $CoQ_{10}$-containing intermediate product. Detailed description related to obtaining the first $CoQ_{10}$-containing intermediate product may be found elsewhere in this disclosure (e.g., FIG. 3, and the description thereof).

In 220, a second $CoQ_{10}$-containing intermediate product may be prepared based on the first $CoQ_{10}$-containing intermediate product. For example, the first $CoQ_{10}$-containing intermediate product obtained in 210 may be transferred to a concentration apparatus for obtaining the concentrate thereof. Merely by way of example, the first $CoQ_{10}$-containing eluate may be transferred to the concentrator 130 to remove the solvent (i.e., all or part of the first eluent) from the eluate to obtain a $CoQ_{10}$-containing concentrate, which is the second $CoQ_{10}$-containing intermediate product. In some embodiments, a commercially available evaporator or the like may be used. For example, the concentrator 130 may include a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof. In some embodiments, purified $CoQ_{10}$ product may be obtained based on the second $CoQ_{10}$-containing intermediate product. For example, the purified $CoQ_{10}$ product may be obtained by concentrating and crystallizing the second $CoQ_{10}$-containing intermediate product. Purity of the $CoQ_{10}$ in the purified $CoQ_{10}$ product was not less than 99.7%.

In 230, a third $CoQ_{10}$-containing intermediate product may be obtained by passing the second $CoQ_{10}$-containing intermediate product through a second chromatographic column. For example, the second $CoQ_{10}$-containing intermediate product may be loaded by the pump 140 to the chromatographic column 150. The second $CoQ_{10}$-containing intermediate product may pass through the chromatographic column 150 (i.e., the second chromatographic column). The second chromatographic column may be eluted by a second eluent. The second eluent to be used to elute the second chromatographic column may include hydrocarbons, fatty acid esters, nitriles, ethers, ketones, alcohols, fatty acids, or the like, or a solution thereof, or any mixture thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination thereof. Exemplary aromatic hydrocarbon may include but not limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane or the like, or a solution thereof, or a combination thereof. In some embodiments, the fatty acid may include but not be limited to propionic acid ester, acetic acid ester, formic acid ester, or the like, or a solution thereof, or a combination thereof. Exemplary propionic acid ester may include but not limited to methyl propionate, ethyl propionate, butyl propionate and isopentyl propionate, or the like, or a solution thereof, or a combination thereof. Exemplary acetic acid ester may include but not limited to methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not limited to acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not limited to acetone, methylethylketone, methyl butyl ketone, methyl isobutyl ketone, or the like, or a solution thereof, or a combination thereof. In some embodiments, the alcohol may be cyclic or non-cyclic. The alcohol may be saturated or unsaturated. Exemplary alcohol may include but not limited to monovalent alcohol, divalent alcohol, trivalent alcohol, or the like, or a solution thereof, or a combination thereof. The monovalent alcohol may include but not limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not be limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. Preferably, the second eluent may include but not be limited to petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a solution thereof, or a combination thereof.

For example, the second eluent may also include hydrocarbons, fatty acid esters, nitriles, ethers, ketones, alcohols, fatty acids, or the like, or a combination thereof. Preferably, the second eluent may include at least one of petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a combination thereof.

The presence of $CoQ_{10}$ in the second eluate may be monitored according to a qualitative analysis method. Exemplary qualitative analysis method for monitoring whether the $CoQ_{10}$ is contained in the second eluate may include the GC, LC, HPLC, TLC, spectrometer analysis method, or the like, or a combination thereof. Alternatively or additionally, the content of the $CoQ_{10}$ contained in the second eluate may be measured based on a quantitative analysis method. Exemplary quantitative analysis method for measuring the content of the $CoQ_{10}$ may include but not be limited to GC, liquid chromatography, HPLC, spectrometer analysis method, or the like, or a combination thereof. The second eluate containing $CoQ_{10}$ may be collected if the second eluate contains the $CoQ_{10}$. The collected second eluate may be concentrated according to a concentration process. In some embodiments, the collected second eluate may be concentrated such that the concentration of the $CoQ_{10}$ in the second eluate reaches or exceeds a predetermined value. The predetermined value may be in a range of 10 to 20 g/L (e.g., 15 g/L). The concentrated second eluate may be designated as the third $CoQ_{10}$-containing intermediate product. Detailed description related to obtaining the third $CoQ_{10}$-containing intermediate product may be found elsewhere in this disclosure (e.g., FIG. 4 and the description thereof). In some embodiments, the second eluate containing $CoQ_{10}$ may be concentrated to dryness to obtain the third $CoQ_{10}$-containing intermediate product, and the purified $CoQ_{10}$ product may be obtained by crystallizing the dried third $CoQ_{10}$-containing intermediate product dissolved in a solution different from the second eluent.

In 240, the purified $CoQ_{10}$ product may be obtained by purifying the third $CoQ_{10}$-containing intermediate product. In some embodiments, a crystallization process may be conducted to obtain the purified $CoQ_{10}$ product. The crystallization process may be carried out by the crystallizer 170. For instance, the third $CoQ_{10}$-containing intermediate product may be dissolved in alcohol having a volume of 10 to 30 times volume of the third $CoQ_{10}$-containing intermediate product. The alcohol may be stirred and heated up to 50 Celsius degrees such that the third $CoQ_{10}$-containing intermediate product may be dissolved therein. The solution may then be cooled down by natural cooling or circulating water, and the solution is monitored to determine whether there is crystal precipitation. For example, crystal precipitation may be observed by a user. If crystals start appearing, the temperature of the solution is maintained for 30 to 180 minutes, after which the solution to be cooled down to 10-30 Celsius degrees. The cooled solution may be aged for 3 hours and may be transferred to a centrifuge to obtain the crystals. The purified $CoQ_{10}$ product may be obtained after drying the crystals.

In some embodiments, the crystallization process may be implemented by an improved crystallization method, for example, vacuum crystallization with adiabatic cooling, solvent-out crystallization, ultrasound crystallization, a continuous crystallization, or the like. Detailed description related to crystallizing the third $CoQ_{10}$-containing intermediate product may be found elsewhere in this disclosure (e.g., in the Examples section below).

In some embodiments, the vacuum crystallization with adiabatic cooling may be carried out for obtaining the purified $CoQ_{10}$ product. For instance, the third $CoQ_{10}$-containing intermediate product may be dissolved in alcohol having a volume of 10 to 15 times volume of the third $CoQ_{10}$-containing intermediate product. The alcohol may be stirred and heated up to 60-70 Celsius degrees such that the third $CoQ_{10}$-containing intermediate product may be dissolved therein. The temperature of the solution may be maintained for 30 minutes, after which the solution may be moved to a vacuum crystallizer. The solution may be concentrated to ½ to ⅓ of the original volume at a negative pressure of 0.07 MPa and a temperature of 18 to 22 Celsius degrees to obtain $CoQ_{10}$ crystals. The concentrated solution may be removed to a centrifuge for separating the $CoQ_{10}$ crystals and mother liquor of the crystallization. The purified $CoQ_{10}$ product may be obtained after the crystals are dried.

In some embodiments, a process based on the solvent-out crystallization may be carried out for obtaining the purified $CoQ_{10}$ product. For instance, the third $CoQ_{10}$-containing intermediate product may be dissolved in ethyl acetate having a volume of 0.5 to 1 times volume of the third $CoQ_{10}$-containing intermediate product. The ethyl acetate may be stirred and heated up to 35-45 Celsius degrees such that the third $CoQ_{10}$-containing intermediate product may be dissolved therein. The temperature of the solution may be maintained for 30 minutes, after which methanol having a volume of 1 to 2 times of the solution may be slowly added into the solution while stirring the solution at a rate of 10 to 15 revolutions per minute. The solution may be cooled down to normal atmospheric temperature under a stirring condition. The cooled solution may be aged for 1.5 hours and may be transferred to a centrifuge to obtain $CoQ_{10}$ crystals. The purified $CoQ_{10}$ product may be obtained after the crystals are dried.

In some embodiments, the ultrasound crystallization may be carried out for obtaining the purified $CoQ_{10}$ product. For instance, the third $CoQ_{10}$-containing intermediate product may be dissolved in alcohol having a volume of 7 to 8 times volume of the third $CoQ_{10}$-containing intermediate product. The alcohol may be stirred and heated up to 55 to 65 Celsius degrees such that the third $CoQ_{10}$-containing intermediate product may be dissolved therein. The temperature of the solution may be maintained for 30 minutes, after which the solution may be cooled down to 45 degrees, after which the solution may immediately be applied ultrasound with a power of 50 to 100 W for 10 minutes. The solution may be cooled down to 18 to 22 degrees Celsius under a stirring condition. The cooled solution may be aged for 1.5 hours and may be transferred to a centrifuge to obtain $CoQ_{10}$ crystals. The purified $CoQ_{10}$ product may be obtained after the crystals are dried.

In some embodiments, the continuous crystallization may be carried out for obtaining the purified $CoQ_{10}$ product. For instance, the third $CoQ_{10}$-containing intermediate product may be dissolved in alcohol having a volume of 7 to 8 times volume of the third $CoQ_{10}$-containing intermediate product. The alcohol may be stirred and heated up to 55 to 65 Celsius degrees such that the third $CoQ_{10}$-containing intermediate product may be dissolved therein. The temperature of the solution may be maintained for 30 minutes, after which the solution may be moved to a first crystallizer by using, for example, a peristaltic pump. The solution may remain in the first crystallizer for 1 to 1.5 hours at a temperature of 37 to 41 Celsius degrees. After that, the solution may be removed from the first crystallizer to a second crystallizer and may remain in the second crystallizer for 1 to 2 hours at the temperature of 16 to 22 Celsius degrees to obtain $CoQ_{10}$ crystals. The solution may be transferred to a centrifuge to obtain the $CoQ_{10}$ crystals. The purified $CoQ_{10}$ product may be obtained after the $CoQ_{10}$ crystals are dried.

In some embodiments, the centrifugation process may include one or more following operations. The solution including $CoQ_{10}$ crystals may be transferred to a centrifuge for centrifuging. The resultant after centrifuging may be washed by using an organic solvent (e.g., alcohol) to obtain the $CoQ_{10}$ crystals. In some embodiments, the residual solution after the centrifugation, which may include $CoQ_{10}$ crystals, may be transferred to one or more additional centrifuges for centrifugation or may wait for a next centrifugation before the last centrifugation complete.

In some embodiments, the $CoQ_{10}$ crystals may be transferred to the dryer 180 to obtain the purified $CoQ_{10}$ product, which is in the form of powders or particles. The $CoQ_{10}$ crystals may be transferred to the dryer 180 by manual or vacuum transfer method. After the transfer is completed, a vacuum pump may be turned on to vacuumize the dryer 180. A main stirrer and a sub-stirrer of the dryer may be turned on. The revolution of the main stirrer may be set to 10 to 50 revolutions per minute, and the revolution of the sub-stirrer may be set to 300 to 600 revolutions per minute. The $CoQ_{10}$ crystals may be dried at a drying temperature of 38 to 42 Celsius degrees for 5 to 8 hours. In some embodiments, the purity (e.g., chromatographic purity) of the purified $CoQ_{10}$ product may be equal to or greater than 99.7%. The content of single impurity (e.g., $CoQ_9$, $CoQ_{10}$ isomeride, or $CoQ_{11}$) may not be more than 0.3%. In some embodiments, the purity (e.g., chromatographic purity) of the purified $CoQ_{10}$ product may be equal to or greater than 99.8%. The content of single impurity (e.g., $CoQ_9$, $CoQ_{10}$ isomeride, or $CoQ_{11}$) may not be more than 0.2%.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 220 and/or operation 230 may be omitted in the exemplary process. The purified $CoQ_{10}$ product may be obtained after passing through a chromatographic column (e.g., a normal-phase chromatographic column) and one or more crystallization operations (e.g., an existing crystallization method or an improved crystallization method).

Figure 3:
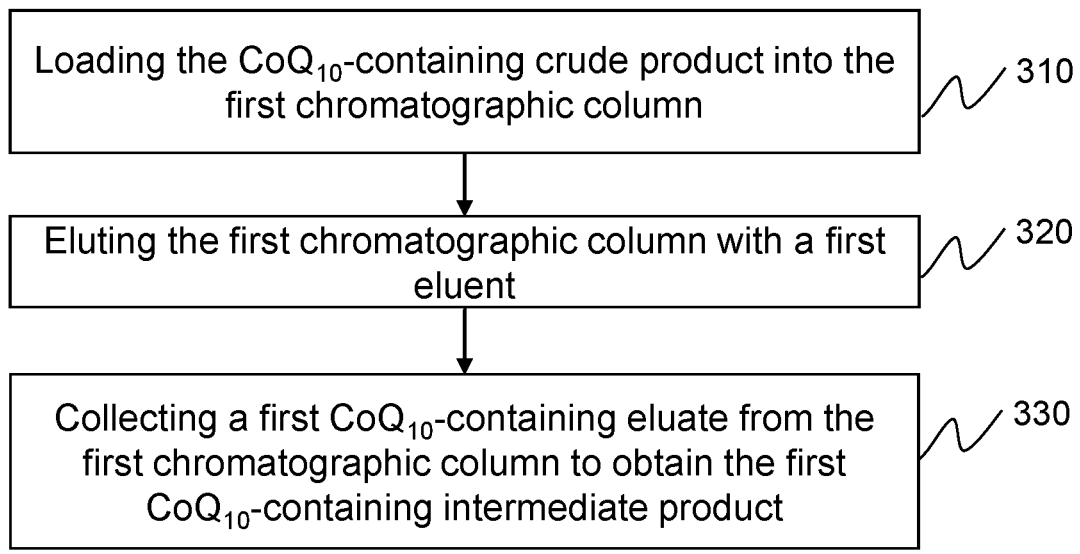
FIG. 3 is a flowchart of an exemplary process for obtaining the first $CoQ_{10}$-containing intermediate product according to some embodiments of the present disclosure.

FIG. 3 is a flowchart of an exemplary process for obtaining the first $CoQ_{10}$-containing intermediate product according to some embodiments of the present disclosure. In some embodiments, one or more steps in the process may be implemented based on the system 100 illustrated in FIG. 1.

In 310, the $CoQ_{10}$-containing crude product may be loaded to the first chromatographic column. In some embodiments, the first chromatographic column may be a normal-phase chromatographic column. The stationary phase of the normal-phase chromatographic column may include but not limited to silica gel, alumina, cellulose powder, bonded phase filler having a polar functional group, or the like, or a combination thereof. In some embodiments, a particle size of the stationary phase of the first chromatographic column may be in a range of 1 μM to 1 mM, preferably in a range of 5 μM to 500 μM, more preferably in a range of 10 μM to 1501 μM. In some embodiments, a loading quantity of the $CoQ_{10}$-containing crude product (e.g., a weight of the $CoQ_{10}$-containing crude product or a volume of the $CoQ_{10}$-containing crude product) may be relative to a quantity of the stationary phase (e.g., a weight of the stationary phase or a volume of the stationary phase) of the first chromatographic column. For example, a weight of pure $CoQ_{10}$ contained in the $CoQ_{10}$-containing crude product to be loaded to the first chromatographic column may be 10 to 30 percent of the weight of the stationary phase. In some embodiments, the $CoQ_{10}$-containing crude product may be loaded to the first chromatographic column by a transfer apparatus (e.g., the pump 110) at a certain flow rate. The flow rate of the $CoQ_{10}$-containing crude product loaded to the first chromatographic column may depend on a volume of the first chromatographic column. For instance, if the volume of the first chromatographic column is V, the flow rate of the $CoQ_{10}$-containing crude product loaded to the first chromatographic column may be V to 3V per hour.

In some embodiments, the first chromatographic column may be a reverse-phase chromatographic column. The stationary phase of the first chromatographic column may include a bonded phase filler having a weak polarity functional group. The bonded phase filler may be a silica gel-based filler, and the weak polarity functional group may be bonded to the surface of the silica gel. In some embodiments, the stationary phase of the first chromatographic column may be the bonded phase filler having an octadecyl group. In some embodiments, a particle size of the stationary phase of the first chromatographic column may be in a range of 1 μM to 1 mM, preferably in a range of 5 μM to 500 μM, more preferably in a range of 10 μM to 150 μM. In some embodiments, a loading quantity of the $CoQ_{10}$-containing crude product (e.g., a weight of the $CoQ_{10}$-containing crude product or a volume of the $CoQ_{10}$-containing crude product) may be relative to a quantity of the stationary phase (e.g., a weight of the stationary phase or a volume of the stationary phase) of the first chromatographic column. For example, a weight of pure $CoQ_{10}$ contained in the $CoQ_{10}$-containing crude product to be loaded into the first chromatographic column may be 10 to 30 percent of the weight of the stationary phase. In some embodiments, the $CoQ_{10}$-containing crude product may be loaded to the first chromatographic column by a transfer apparatus (e.g., the pump 140) at a certain flow rate. The flow rate of the $CoQ_{10}$-containing crude product may be depend on the volume of the first chromatographic column. If the volume of the first chromatographic column is V the loading flow velocity may be determined as 1 to 3 times V per hour.

In 320, the first chromatographic column may be eluted by a first eluent. The first eluent may include but not limited to hydrocarbons, fatty acid esters, nitriles, ethers, ketones, alcohols, fatty acids, or the like, or a solution thereof, or a combination thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination thereof. Exemplary aromatic hydrocarbon may include but not limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane or the like, or a solution thereof, or a combination thereof. In some embodiments, the fatty acid may include but not limited to propionic acid ester, acetic acid ester, formic acid ester, or the like, or a solution thereof, or a combination thereof. Exemplary propionic acid ester may include but not limited to methyl propionate, ethyl propionate, butyl propionate and isopentyl propionate, or the like, or a solution thereof, or a combination thereof. Exemplary acetic acid ester may include but not limited to methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not limited to acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not limited to acetone, methylethylketone, methyl butyl ketone, methyl isobutyl ketone, or the like, or a solution thereof, or a combination thereof. In some embodiments, the alcohol may be cyclic or non-cyclic. The alcohol may be saturated or unsaturated. Exemplary alcohol may include but not limited to monovalent alcohol, divalent alcohol, trivalent alcohol, or the like, or a solution thereof, or a combination thereof. The monovalent alcohol may include but not limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. In some embodiments, the first eluent may include but not limited to petroleum ether, n-hexane, n-heptane, benzene, diethyl ether, isopropyl ether, isopropanol, ethyl acetate, acetone, butanone, dichioromethane, trichloroethane, n-butyl alcohol, alcohol, methanol, water, or the like, or a solution thereof, or a combination thereof.

In some embodiments, when the first chromatographic column is a normal-phase chromatographic column, the first eluent may be a normal-phase eluent. The normal-phase eluent may include but not limited to one or more solvents selected from a group consisting of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, methanol, ethanol, n-propanol, isopropanol, n-butanol, isobutanol, acetonitrile, or the like. Preferably, the normal-phase eluent may be a mixture of a first solvent and a second solvent. The first solvent may include at least one of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, or the like, or a combination thereof. The second solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, methanol, ethanol, n-propanol, isopropanol, n-butanol, isobutanol, or acetonitrile, or the like, or a combination thereof.

The amounts of the solvents mentioned above may not be particularly limited. Preferably, a volume of the second solvent may be in a range of 1% to 50% by volume relative to a total volume of the normal-phase eluent. More preferably, the volume of the second solvent may be in a range of 2% to 10% by volume relative to the total volume of the normal-phase eluent.

In some embodiments, when the first chromatographic column is a reverse-phase chromatographic column, the first eluent may be a reverse-phase eluent. The reverse-phase eluent may include but not limited to one or more solvents selected from petroleum ether, n-hexane, n-heptane, benzene, diethyl ether, isopropyl ether, isopropanol, ethyl acetate, acetone, butanone, dichloromethane, trichloroethane, methyl acetate, propyl acetate, isopropyl acetate, butyl acetate, methyl propionate, ethyl propionate, butyl propionate, diethyl ether, isopropyl ether, acetone, n-propanol, isopropanol, n-butanol, isobutanol, n-butyl alcohol, alcohol, methanol, water, or the like. Preferably, the reverse-phase eluent may be mixture of a fourth solvent and a fifth solvent. The fourth solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, n-propanol, isopropanol, n-butanol, isobutanol, or the like, or a combination thereof. The fifth solvent may include at least one of alcohol, methanol, acetonitrile, or water, or the like, or a combination thereof.

The amounts of the solvents mentioned above to be used may be not particularly limited. Preferably, a volume of the third solvent may be in a range of 10% to 90% by volume relative to a total volume of the reverse-phase eluent. More preferably, the volume of the fourth solvent may be in a range of 20% to 60% by volume relative to the total volume of the reverse-phase eluent.

In some embodiments, a first flow rate of the first eluent may depend on the volume of the first chromatographic column. For instance, if the volume of the first chromatographic column is V, the first flow rate of the first eluent eluting the first chromatographic column may be V to 3V per hour.

In order to provide a stationary phase of the first chromatographic column with an excellent density and stability, the pressure of the first chromatographic column may be kept in a range from 3 to 300 bar. In some embodiments, the range in which the pressure of the first chromatographic column is maintained may be restricted in a subrange of 30 to 300 bar. It may also effectively prevent the collapse of the stationary phase while ensuring high separation efficiency and consistency of separation effect for long-term use.

In 330, a first $CoQ_{10}$-containing eluate from the first chromatographic column may be collected.

In some embodiments, an eluate may be referred to as the eluent coming out of the chromatographic column, which may contain all or parts of elements in the loaded sample. In the process of elution, the presence of $CoQ_{10}$ in an eluate which received from the first chromatographic column may be monitored according to a qualitative analysis method. Exemplary qualitative analysis method for monitoring the presence of $CoQ_{10}$ in the first eluate may include but not limited to the MS, NMR, IR, UV/Vis, GC, LC, HPLC, TLC, LC-MS, or the like, or a combination thereof. In some embodiments, TLC may be used to monitor the presence of $CoQ_{10}$ in the eluate which received from the first chromatographic column. The developing solvent to be used for TLC may not be particularly limited, and may only need to be selected according to the $CoQ_{10}$. The developing solvent may include hydrocarbons, fatty acid esters, nitriles, ethers, ketones, alcohols, fatty acids, or the like, or a combination thereof. In some embodiments, after every regular interval, for example, 1 minute, 2 minutes, 3 minutes, or the like, a newly eluate received from the first chromatographic column may be tested by TLC. If the eluate contains $CoQ_{10}$, the eluate obtained during the interval may be collected. The collected eluate may be designated as the first $CoQ_{10}$-containing eluate.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in 320, the first chromatographic column may be a reverse-phase chromatographic column. It may also achieve the purpose of separation and purification.

Figure 4:
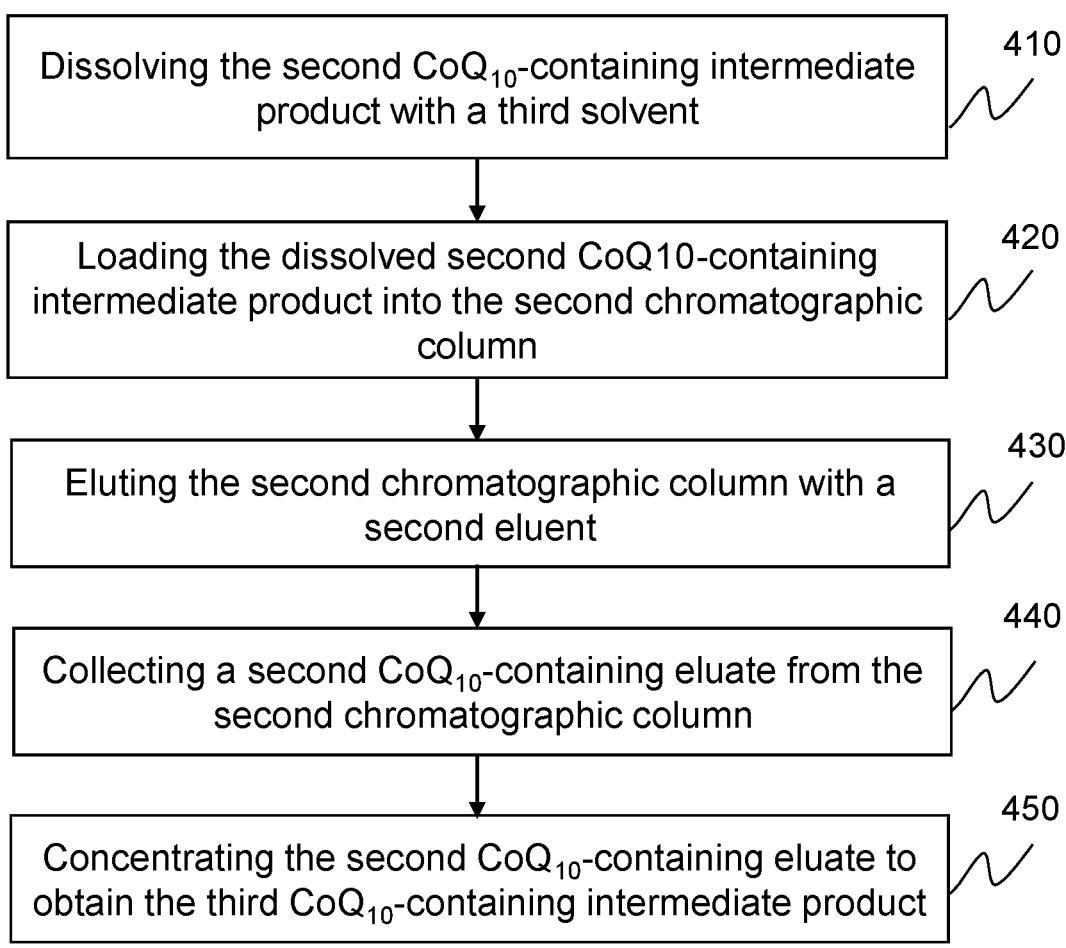
FIG. 4 is a flowchart of an exemplary process for obtaining the third $CoQ_{10}$-containing intermediate product according to some embodiments of the present disclosure.

FIG. 4 is a flowchart of an exemplary process for obtaining the third $CoQ_{10}$-containing intermediate product according to some embodiments of the present disclosure. In some embodiments, one or more steps in the process may be implemented based on the system 100 illustrated in FIG. 1.

In 410, the second $CoQ_{10}$-containing intermediate product may be dissolved in a third solvent. In some embodiments, one or more methods may be utilized to promote the dissolution of the second $CoQ_{10}$-containing intermediate product, for example, stirring and/or heating. In some embodiments, the dissolved second $CoQ_{10}$-containing intermediate product may have a predetermined concentration. The predetermined concentration may be in a range of 0.1 to 0.3 g/mL (e.g., 0.2 g/mL). The volume of the third solvent to be used for dissolving the second $CoQ_{10}$-containing intermediate product may be relative to the predetermined concentration and the weight of the second $CoQ_{10}$-containing intermediate product. In some embodiments, when the second chromatographic column is the reverse-phase chromatographic column, the third solvent may include petroleum ether, methanol, alcohol, ethyl acetate, acetone, butanone, dichloromethane, trichloroethane, n-hexane, diethyl ether, isopropyl ether, isopropanol, acetonitrile, water, methyl acetate, propyl acetate, isopropyl acetate, butyl acetate, methyl propionate, ethyl propionate, butyl propionate, diethyl ether, n-propanol, isopropanol, n-butanol, isobutanol, or the like, or a combination thereof. In some embodiments, the third solvent may be a mixed solvent. One part of the third solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, n-propanol, isopropanol, n-butanol, or isobutanol. Another part of the third solvent may include at least one of alcohol, methanol, acetonitrile, or water. In some embodiments, the volume of the at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, n-propanol, isopropanol, n-butanol, or isobutanol may be in a range of 40% to 90% by volume relative to the total volume of the third solvent.

In some embodiments, when the second chromatographic column is the normal-phase chromatographic column, the third solvent may be same as the normal-phase eluent.

In 420, the dissolved second $CoQ_{10}$-containing intermediate product may be loaded to the second chromatographic column. In some embodiments, the second chromatographic column may be a reverse-phase chromatographic column. The stationary phase of the second chromatographic column may include a bonded phase filler having a weak polarity functional group. The bonded phase filler may be a silica gel-based filler, and the weak polarity functional group may be bonded to the surface of the silica gel. In some embodiments, the stationary phase of the second chromatographic column may be the bonded phase filler having an octadecyl group. In some embodiments, a particle size of the stationary phase of the second chromatographic column may be in a range of 1 μM to 1 mM, preferably in a range of 5 μM to 500 μM, more preferably in a range of 10 μM to 150 μM. In some embodiments, a loading quantity of the dissolved second $CoQ_{10}$-containing intermediate product (e.g., a weight of the dissolved second $CoQ_{10}$-containing intermediate product or a volume of the dissolved second $CoQ_{10}$-containing intermediate product) may be relative to a quantity of the stationary phase (e.g., a weight of the stationary phase or a volume of the stationary phase) of the second chromatographic column. For example, a weight of pure $CoQ_{10}$ contained in the dissolved second $CoQ_{10}$-containing intermediate product to be loaded into the second chromatographic column may be 5 to 20 percent of the weight of the stationary phase.

In some embodiments, the dissolved second $CoQ_{10}$-containing intermediate product may be loaded to the second chromatographic column by a transfer apparatus (e.g., the pump 140) at a certain flow rate. The flow rate of the dissolved second $CoQ_{10}$-containing intermediate product may be depend on the volume of the second chromatographic column. If the volume of the second chromatographic column is V', the loading flow velocity may be determined as 1 to 3 times V' per hour.

In some embodiments, the second chromatographic column may be a normal-phase chromatographic column. The stationary phase of the second chromatographic column may include but not limited to silica gel, alumina, cellulose powder, bonded phase filler having a polar functional group, or the like, or a combination thereof. In some embodiments, a particle size of the stationary phase of the second chromatographic column may be in a range of 1 μM to 1 mM, preferably in a range of 5 μM to 500 μM, more preferably in a range of 10 μM to 1501 μM. In some embodiments, a loading quantity of the dissolved second $CoQ_{10}$-containing intermediate product (e.g., a weight of the dissolved second $CoQ_{10}$-containing intermediate product or a volume of the dissolved second $CoQ_{10}$-containing intermediate product) may be relative to a quantity of the stationary phase (e.g., a weight of the stationary phase or a volume of the stationary phase) of the second chromatographic column. For example, a weight of pure $CoQ_{10}$ contained in the the dissolved second $CoQ_{10}$-containing intermediate product to be loaded to the second chromatographic column may be 5 to 20 percent of the weight of the stationary phase. In some embodiments, the dissolved second $CoQ_{10}$-containing intermediate product may be loaded to the second chromatographic column by a transfer apparatus (e.g., the pump 110) at a certain flow rate. The flow rate of the dissolved second $CoQ_{10}$-containing intermediate product loaded to the second chromatographic column may depend on a volume of the second chromatographic column. For instance, if the volume of the second chromatographic column is V', the flow rate of the dissolved second $CoQ_{10}$-containing intermediate product loaded to the first chromatographic column may be V' to 3 V' per hour.

In 430, the second chromatographic column may be eluted with a second eluent. The second eluent may include but not limited to hydrocarbons, fatty acid esters, nitriles, ethers, ketones, alcohols, fatty acids, or the like, or a solution thereof, or a combination thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination mixture thereof. Exemplary aromatic hydrocarbon may include but not limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane or the like, or a solution thereof, or a combination thereof. In some embodiments, the fatty acid may include but not limited to propionic acid ester, acetic acid ester, formic acid ester, or the like, or a solution thereof, or a combination thereof. Exemplary propionic acid ester may include but not limited to methyl propionate, ethyl propionate, butyl propionate and isopentyl propionate, or the like, or a solution thereof, or a combination thereof. Exemplary acetic acid ester may include but not limited to methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not limited to acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not limited to acetone, methylethylketone, methyl butyl ketone, methyl isobutyl ketone, or the like, or a solution thereof, or a combination thereof. In some embodiments, the alcohol may be cyclic or non-cyclic. The alcohol may be saturated or unsaturated. Exemplary alcohol may include but not limited to monovalent alcohol, divalent alcohol, trivalent alcohol, or the like, or a solution thereof, or a combination thereof. The monovalent alcohol may include but not limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. Preferably, the second eluent may include but not limited to petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a solution thereof, or a combination thereof.

In some embodiments, when the second chromatographic column is a reverse-phase chromatographic column, the second eluent may be the reverse-phase eluent. The reverse-phase eluent may include but not limited to one or more solvents selected from a group consisting of petroleum ether, n-hexane, n-heptane, benzene, diethyl ether, isopropyl ether, isopropanol, ethyl acetate, acetone, butanone, dichloromethane, trichloroethane, methyl acetate, propyl acetate, isopropyl acetate, butyl acetate, methyl propionate, ethyl propionate, butyl propionate, diethyl ether, isopropyl ether, acetone, n-propanol, isopropanol, n-butanol, isobutanol, n-butyl alcohol, alcohol, methanol, water, or the like. Preferably, the second eluent may be a mixture of a fourth solvent and a fifth solvent. The fourth solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, n-propanol, isopropanol, n-butanol, isobutanol, or the like, or a combination thereof. The fifth solvent may include at least one of alcohol, methanol, acetonitrile, or water, or the like, or a combination thereof.

The amounts of the solvents mentioned above to be used may be not particularly limited. Preferably, a volume of the fourth solvent may be in a range of 10% to 90% by volume relative to a total volume of the reverse-phase eluent. More preferably, the volume of the fourth solvent may be in a range of 20% to 60% by volume relative to the total volume of the reverse-phase eluent. In some embodiments, the volume of the fourth solvent may be in a range of 20% to 30% by volume relative to the total volume of the reverse-phase eluent.

In some embodiments, when the second chromatographic column is a normal-phase chromatographic column, the second eluent may be the normal-phase eluent. The normal-phase eluent may include but not limited to one or more solvents selected from a group consisting of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, methanol, ethanol, n-propanol, isopropanol, n-butanol, isobutanol, acetonitrile, or the like. Preferably, the normal-phase eluent may be a mixture of the first solvent and the second solvent. The first solvent may include at least one of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, or the like, or a combination thereof. The second solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, methanol, ethanol, n-propanol, isopropanol, n-butanol, isobutanol, or acetonitrile, or the like, or a combination thereof.

The amounts of the solvents mentioned above may not be particularly limited. Preferably, a volume of the second solvent may be in a range of 1% to 50% by volume relative to a total volume of the normal-phase eluent. More preferably, the volume of the second solvent may be in a range of 2% to 10% by volume relative to the total volume of the normal-phase eluent.

In some embodiments, a flow rate of the second eluent may be depend on the volume of the second chromatographic column. For instance, if the volume of the second chromatographic column is V', the flow rate of the second eluent loaded into the first chromatographic column may be in a range from V' to 3V per hour.

In order to provide a stationary phase of the second chromatographic column with an excellent density and stability, a pressure of the second chromatographic column may be maintained in a range from 3 to 300 bars. In some embodiments, the range in which the pressure of the second chromatographic column is maintained may be restricted in a subrange of 30 to 300 bar. It may also effectively prevent the collapse of the stationary phase while ensuring high separation efficiency and consistency of separation effect for long-term use.

In 440, a second $CoQ_{10}$-containing eluate from the second chromatographic column may be collected. In some embodiments, an eluate may be referred to as the eluent coming out of the chromatographic column, which may contain all or parts of elements in the loaded sample. In the process of elution, the presence of $CoQ_{10}$ in an eluate which received from the first chromatographic column may be monitored according to a qualitative analysis method. Exemplary qualitative analysis method for monitoring the presence of $CoQ_{10}$ in the first eluate may include but not limited to the (MS, NMR), IR, UV/Vis, GC, LC, HPLC, TLC, LC-MS, or the like, or a combination thereof. In some embodiments, TLC may be used to monitor the presence of $CoQ_{10}$ in the eluate which received from the first chromatographic column. The developing solvent to be used for TLC may not be particularly limited, and may only need to be selected according to the $CoQ_{10}$. The developing solvent may include hydrocarbons, fatty acid esters, nitriles, ethers, ketones, alcohols, fatty acids, or the like, or a combination thereof. In some embodiments, after every regular interval, for example, 1 minute, 2 minutes, 3 minutes, or the like, a newly eluate received from the second chromatographic column may be tested by TLC. If the eluate contains $CoQ_{10}$, the eluate obtained during the interval may be collected. The collected eluate may be designated as the second $CoQ_{10}$-containing eluate.

In 450, the third $CoQ_{10}$-containing intermediate product may be obtained by concentrating the second $CoQ_{10}$-containing eluate. In some embodiments, the second $CoQ_{10}$-containing eluate may be transferred to a concentration apparatus, for instance, an evaporator, for concentrating. Merely by way of example, a commercially available evaporator or the like may be used. The evaporator may include a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof. In some embodiments, the concentration process may be ended when the solid content of the residual second $CoQ_{10}$-containing eluate reaches 10 to 20 g/L. When the condition mentioned above is satisfied, the residual second $CoQ_{10}$-containing eluate after the centrifugation may be collected and designated as the third $CoQ_{10}$-containing intermediate product.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in 420, the second chromatographic column may be a normal-phase chromatographic column. It may also achieve the purpose of separation and purification.

Figure 5:
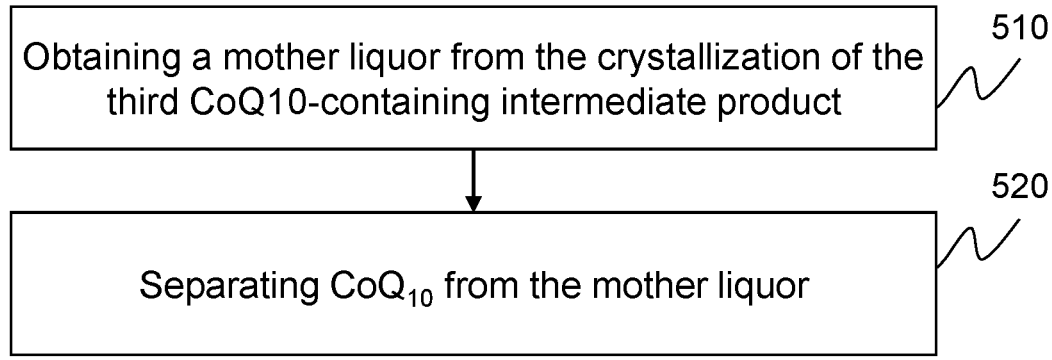
FIG. 5 is a flowchart of an exemplary process for separating $CoQ_{10}$ from a mother liquor according to some embodiments of the present disclosure.

FIG. 5 is a flowchart of an exemplary process for separating $CoQ_{10}$ from a mother liquor according to some embodiments of the present disclosure. In some embodiments, one or more steps in the process may be implemented based on the system 100 illustrated in FIG. 1.

In 510, a mother liquor from the crystallization may be obtained. In some embodiments, the mother liquor may be referred to as a crystallization solution that is separated from the crystal. The separation process may be conducted by a centrifuge. For instance, after centrifuging, the crystals may be removed from the crystallization solution and residual crystallization solution may be obtained and designated as the mother liquor. In some embodiments, the mother liquor may include crystallization solvent, non-crystallized $CoQ_{10}$, and/or other impurities, for instance, $CoQ_9$, $CoQ_{10}$ isomeride, and $CoQ_{11}$. Therefore, the mother liquor may need to be further processed to obtain the non-crystallized $CoQ_{10}$. Separating $CoQ_{10}$ from the mother liquor may improve the yield of the $CoQ_{10}$ in the whole purification process.

In 520, the $CoQ_{10}$ may be separated from the mother liquor. In some embodiments, chromatography and/or crystallization may be used to separate $CoQ_{10}$ from the mother liquor. For example, the mother liquor may be loaded to and pass through a normal-phase chromatographic column. The $CoQ_{10}$-containing eluate collected from the normal-phase chromatographic column or a concentrate thereof (obtained after the $CoQ_{10}$-containing eluate undergoes a concentration process) may be designated as a fourth $CoQ_{10}$-containing intermediate product. Then, the $CoQ_{10}$ may be obtained by crystallizing the fourth $CoQ_{10}$-containing intermediate product several times (e.g., three times) by using a crystallization method. Alternatively or additionally, the mother liquor may be loaded to and pass through a reverse-phase chromatographic column. The $CoQ_{10}$-containing eluate collected from the reverse-phase chromatographic column or the concentrate thereof (obtained after the $CoQ_{10}$-containing eluate undergo a concentration process) may be designated as the fourth $CoQ_{10}$-containing intermediate product. Then, the $CoQ_{10}$ may be obtained by crystallizing the fourth $CoQ_{10}$-containing intermediate product by using an improved crystallization method. Alternatively or additionally, the mother liquor may be loaded to and pass through a normal-phase chromatographic column, and a $CoQ_{10}$-containing normal-phase eluate may be collected from the normal-phase chromatographic column. Then, the $CoQ_{10}$-containing normal-phase eluate may be loaded to and pass through a reverse-phase chromatographic column directly or after being concentrated, and a $CoQ_{10}$-containing reverse-phase eluate may be collected from the reverse-phase chromatographic column. The $CoQ_{10}$ may be obtained by crystallizing the $CoQ_{10}$-containing reverse-phase eluate or a concentrate of the $CoQ_{10}$-containing reverse-phase eluate several times (e.g., three times) by using a crystallization method. Alternatively or additionally, the mother liquor may be loaded to and pass through a normal-phase chromatographic column, and a $CoQ_{10}$-containing normal-phase eluate may be collected from the normal-phase chromatographic column. Then, the $CoQ_{10}$-containing normal-phase eluate may be loaded to and pass through a reverse-phase chromatographic column directly or after being concentrated, and a $CoQ_{10}$-containing reverse-phase eluate may be collected from the reverse-phase chromatographic column. The $CoQ_{10}$ may be obtained by crystallizing the $CoQ_{10}$-containing reverse-phase eluate or a concentrate thereof (obtained after the $CoQ_{10}$-containing reverse-phase eluate undergoes a concentration process) by using an improved crystallization method. Alternatively or additionally, the mother liquor may be loaded to and pass through a reverse-phase chromatographic column, and a $CoQ_{10}$-containing reverse-phase eluate may be collected from the reverse-phase chromatographic column. Then, the $CoQ_{10}$-containing reverse-phase eluate may be loaded to and pass through a normal-phase chromatographic column directly or after being concentrated, and a $CoQ_{10}$-containing normal-phase eluate may be collected from the normal-phase chromatographic column. The $CoQ_{10}$ may be obtained by crystallizing the $CoQ_{10}$-containing normal-phase eluate or a concentrate of the $CoQ_{10}$-containing normal-phase eluate several times (e.g., three times) by using a crystallization method.

Alternatively or additionally, the mother liquor may be loaded to and pass through a reverse-phase chromatographic column, and a $CoQ_{10}$-containing reverse-phase eluate may be collected from the reverse-phase chromatographic column. Then, the $CoQ_{10}$-containing reverse-phase eluate may be loaded to and pass through a normal-phase chromatographic column directly or after being concentrated, and a $CoQ_{10}$-containing normal-phase eluate may be collected from the normal-phase chromatographic column. The $CoQ_{10}$ may be obtained by crystallizing the $CoQ_{10}$-containing normal-phase eluate or a concentrate thereof (obtained after the $CoQ_{10}$-containing normal-phase eluate undergoes a concentration process) by using an improved crystallization method. The detail of a preferred separation process may be found elsewhere in this disclosure (e.g., FIG. 6 and the descriptions thereof).

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
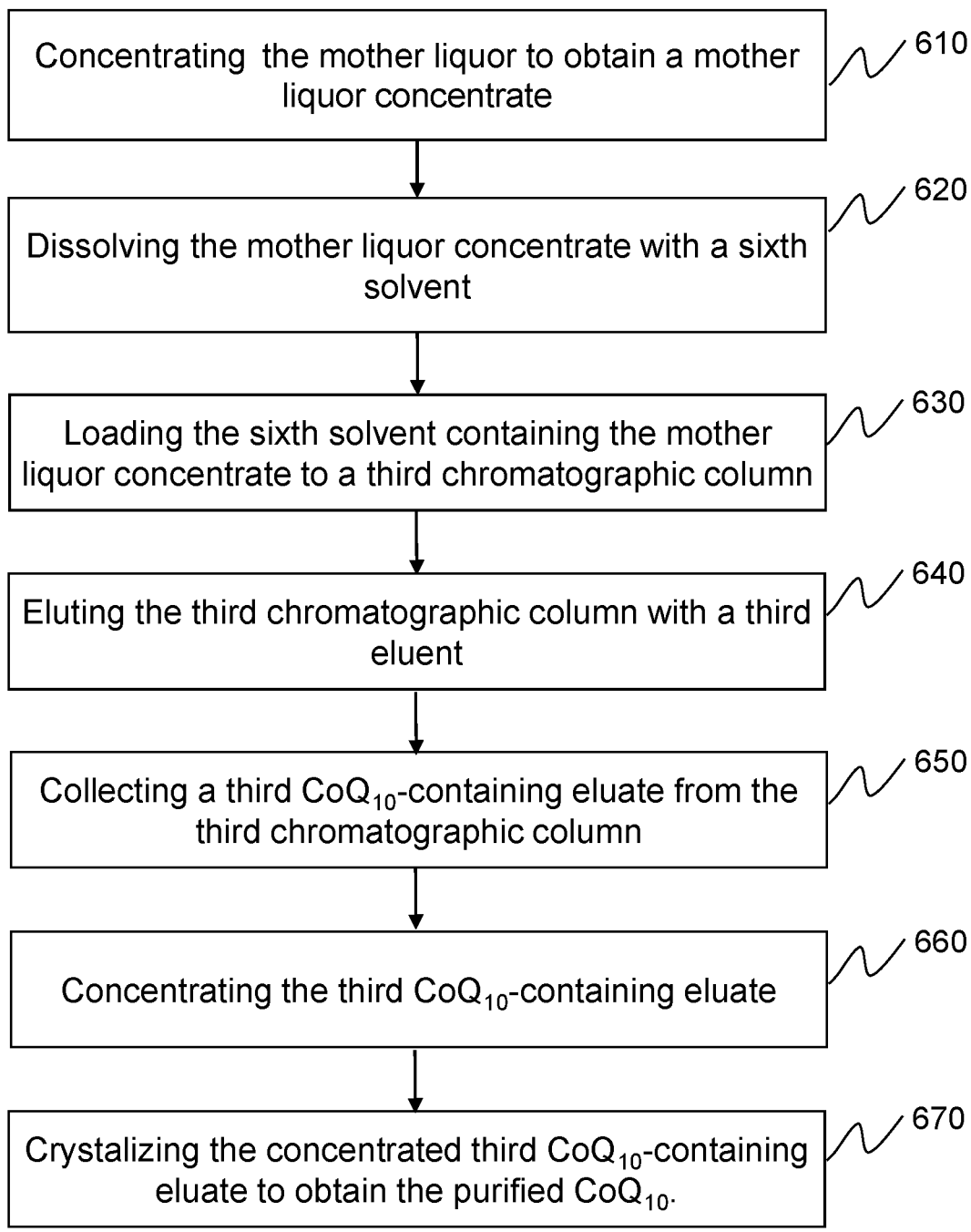
FIG. 6 is a flowchart of an exemplary process for separating $CoQ_{10}$ from a mother liquor according to some embodiments of the present disclosure.

FIG. 6 is a flowchart of an exemplary process for separating $CoQ_{10}$ from a mother liquor according to some embodiments of the present disclosure. In some embodiments, one or more steps in the process may be implemented based on the system 100 illustrated in FIG. 1.

In 610, a mother liquor concentrate may be obtained by concentrating the mother liquor. The concentration process may be implemented by, for example, an evaporator. Merely by way of example, the evaporator may include a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof. The mother liquor concentrate may be obtained by removing the crystallization solvent.

In 620, the mother liquor concentrate may be dissolved in a sixth solvent. In some embodiments, the dissolution process may be similar to the description found elsewhere in this disclosure, for example, operation 410 of process 400 illustrated in FIG. 4. Similarly, stirring and/or heating may be utilized to promote the dissolution of the mother liquor concentrate. The dissolved mother liquor concentrate may also have a predetermined concentration. The predetermined concentration may be in a range of 0.2 to 0.5 g/mL (e.g., 0.4 g/mL). In some embodiments, the sixth solvent may include petroleum ether, methanol, alcohol, ethyl acetate, acetone, butanone, dichloromethane, trichloroethane, n-hexane, diethyl ether, isopropyl ether, isopropanol, acetonitrile, water, or the like. In some embodiments, the sixth solvent may be a mixed solvent. One part of the sixth solvent may include at least one of acetone, ethyl acetate, or butanone. Another part of the sixth solvent may include at least one of alcohol, methanol, or water. In some embodiments, the volume of the at least one of acetone, ethyl acetate, or butanone may be in a range of 40% to 90% by volume relative to the total volume of the sixth solvent.

In 630, the dissolved mother liquor concentrate may be loaded to and pass through a third chromatographic column.

In some embodiments, the third chromatographic column may be a reverse-phase chromatographic column. The stationary phase of the third chromatographic column may include a bonded phase filler having a weak polarity functional group. The bonded phase filler may be a silica gel-based filler, and the weak polarity functional group may be bonded to the surface of the silica gel. In some embodiments, the stationary phase of the third chromatographic column may be the bonded phase filler having an octadecyl group. In some embodiments, a particle size of the stationary phase of the third chromatographic column may be in a range of 1 µM to 1 mM, preferably in a range of 5 µM to 500 µM, more preferably in a range of 10 µM to 150 µM. In some embodiments, a loading quantity of the dissolved mother liquor concentrate (e.g., a weight of the mother liquor concentrate or a volume of the mother liquor concentrate) may depend on the quantity of the stationary phase (e.g., a weight of the stationary phase or a volume of the stationary phase) of the third chromatographic column. For example, a weight of pure $CoQ_{10}$ contained in the dissolved mother liquor concentrate product to be loaded into the third chromatographic column may be 2.5 to 10 percent of the weight of the stationary phase. In some embodiments, the dissolved mother liquor concentrate may be loaded to the third chromatographic column by a transfer apparatus, for example, the pump 110.

In some embodiments, a flow rate of the dissolved mother liquor concentrate may depend on the volume of the third chromatographic column. For instance, if the volume of the third chromatographic column is V''', the flow rate of the mother liquor concentrate into the third chromatographic column may be set in a range from V''' to 3V''' per hour.

In some embodiments, the third chromatographic column may be a normal-phase chromatographic column. The stationary phase of the third chromatographic column may include but not limited to silica gel, alumina, cellulose powder, bonded phase filler having a polar functional group, or the like, or a combination thereof. In some embodiments, a particle size of the stationary phase of the second chromatographic column may be in a range of 1 µM to 1 mM, preferably in a range of 5 µM to 500 µM, more preferably in a range of 10 µM to 150 µM. In some embodiments, a loading quantity of the dissolved mother liquor concentrate (e.g., a weight of the mother liquor concentrate or a volume of the mother liquor concentrate) may be relative to a quantity of the stationary phase (e.g., a weight of the stationary phase or a volume of the stationary phase) of the third chromatographic column. For example, a weight of pure $CoQ_{10}$ contained in the the dissolved mother liquor concentrate product to be loaded to the third chromatographic column may be 5 to 20 percent of the weight of the stationary phase. In some embodiments, the dissolved mother liquor concentrate product may be loaded to the third chromatographic column by a transfer apparatus (e.g., the pump 110) at a certain flow rate. The flow rate of the dissolved mother liquor concentrate product loaded to the third chromatographic column may depend on a volume of the third chromatographic column. For instance, if the volume of the third chromatographic column is V''', the flow rate of the dissolved mother liquor concentrate product loaded to the first chromatographic column may be V''' to 3 V''' per hour.

In 640, the third chromatographic column may be eluted with a third eluent. The third eluent may include but not limited to hydrocarbons, fatty acid esters, nitriles, ethers, ketones, alcohols, fatty acids, or the like, or a solution thereof, or a combination thereof. In some embodiments, the hydrocarbons may include but not limited to aliphatic hydrocarbon, aromatic hydrocarbon, halogenated hydrocarbon, or the like, or a solution thereof, or a combination thereof. The aliphatic hydrocarbon may be cyclic or non-cyclic, saturated or unsaturated. Exemplary aliphatic hydrocarbons may include but not limited to propane, butane, isobutane, pentane, 2-methylbutane, cyclopentane, 2-pentene, n-hexane, 2-methylpentane, 2,2-dimethylbutane, 2,3-dimethylbutane, methylcyclopentane, cyclohexane, 1-hexene, cyclohexene, n-heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane, or the like, or a solution thereof, or a combination thereof. Exemplary aromatic hydrocarbon may include but not limited to benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, or the like, or a solution thereof, or a combination thereof. The halogenated hydrocarbon may be cyclic or non-cyclic. The halogenated hydrocarbon may be saturated or unsaturated. Exemplary halogenated hydrocarbon may include but not limited to dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane or the like, or a solution thereof, or a combination thereof. In some embodiments, the fatty acid may include but not limited to propionic acid ester, acetic acid ester, formic acid ester, or the like, or a solution thereof, or a combination thereof. Exemplary propionic acid ester may include but not limited to methyl propionate, ethyl propionate, butyl propionate and isopentyl propionate, or the like, or a solution thereof, or a combination thereof. Exemplary acetic acid ester may include but not limited to methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, or the like, or a solution thereof, or a combination thereof. Exemplary formic acid ester may include but not limited to methyl formate, ethyl formate, propyl formate, isopropyl formate, butyl formate, isobutyl formate, sec-butyl formate, pentylformate, or the like, or a solution thereof, or a combination thereof. In some embodiments, the nitrile may be cyclic or non-cyclic. The nitrile may be saturated or unsaturated. Exemplary nitrile may include but not limited to acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, cyanomethyl acetate, cyanoethyl acetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile, or the like, or a solution thereof, or a combination thereof. In some embodiments, the ester may be cyclic or non-cyclic. The ester may be saturated or unsaturated. Exemplary ester may include but not limited to diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether, or the like, or a solution thereof, or a combination thereof. In some embodiments, exemplary ketone may include but not limited to acetone, methylethylketone, methyl butyl ketone, methyl isobutyl ketone, or the like, or a solution thereof, or a combination thereof. In some embodiments, the alcohol may be cyclic or non-cyclic. The alcohol may be saturated or unsaturated. Exemplary alcohol may include but not limited to monovalent alcohol, divalent alcohol, trivalent alcohol, or the like, or a solution thereof, or a combination thereof. The monovalent alcohol may include but not limited to methanol, ethanol, 1-propanol, 2-propanol, 1-butanol, 2-butanol, isobutylalcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzylalcohol, cyclohexanol, 1-methylcyclohexanol, 2-methylcyclohexanol, 3-methylcyclohexanol, 4-methylcyclohexanol, or the like, or a solution thereof, or a combination thereof. Exemplary divalent alcohol may include but not limited to 1,2-ethanediol, 1,2-propanediol, 1,3-propanediol, 1,2-butanediol, 1,3-butanediol, 1,4-butanediol, 2,3-butanediol, 1,5-pentanediol, or the like, or a solution thereof, or a combination thereof. Exemplary trivalent alcohol may include glycerol and the like. Preferably, the third eluent may include but not limited to petroleum ether, n-hexane, n-heptane, benzene, diethyl ether, isopropyl ether, isopropanol, ethyl acetate, acetone, butanone, dichloromethane, trichloroethane, n-butyl alcohol, alcohol, methanol, water, or the like, or a solution thereof, or a combination thereof.

In some embodiments, the third eluent may be the reverse-phase eluent. The reverse-phase eluent may include but not be limited to one or more solvents selected from a group consisting of petroleum ether, n-hexane, n-heptane, benzene, diethyl ether, isopropyl ether, isopropanol, ethyl acetate, acetone, butanone, dichloromethane, trichloroethane, methyl acetate, propyl acetate, isopropyl acetate, butyl acetate, methyl propionate, ethyl propionate, butyl propionate, diethyl ether, isopropyl ether, acetone, n-propanol, isopropanol, n-butanol, isobutanol, n-butyl alcohol, alcohol, methanol, water, or the like. Preferably, the third eluent may be a mixture of the fourth solvent and the fifth solvent. The fourth solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, n-propanol, isopropanol, n-butanol, isobutanol, or the like, or a mixture thereof. The fifth solvent may include at least one of alcohol, methanol, acetonitrile, or water, or the like, or a combination thereof.

The amounts of the solvents mentioned above to be used may be not particularly limited. Preferably, a volume of the fourth solvent may be in a range of 10% to 90% by volume relative to a total volume of the reverse-phase eluent. More preferably, the volume of the fourth solvent may be in a range of 20% to 60% by volume relative to the total volume of the reverse-phase eluent. In some embodiments, the volume of the fourth solvent may be in a range of 20% to 30% by volume relative to the total volume of the reverse-phase eluent.

In some embodiments, the third eluent may be the normal-phase eluent. The normal-phase eluent may include but not limited to one or more solvents selected from a group consisting of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, dichloromethane, methyl acetate, ethyl acetate, propyl acetate, isopropyl acetate, butyl acetate, methyl propionate, ethyl propionate, butyl propionate, diethyl ether, isopropyl ether, acetone, methanol, ethanol, n-propanol, isopropanol, n-butanol, isobutanol, acetonitrile, or the like. Preferably, the normal-phase eluent may be a mixture of the first solvent and the second solvent. The first solvent may include at least one of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, 1-octene, or the like, or a combination thereof. The second solvent may include at least one of dichloromethane, methyl acetate, ethyl acetate, propyl acetate, isopropyl acetate, butyl acetate, methyl propionate, ethyl propionate, butyl propionate, diethyl ether, isopropyl ether, acetone, methylethylketone, methanol, ethanol, n-propanol, isopropanol, n-butanol, isobutanol, or acetonitrile, or the like, or a combination thereof.

The amounts of the solvents mentioned above may not be particularly limited. Preferably, a volume of the second solvent may be in a range of 1% to 50% by volume relative to a total volume of the normal-phase eluent. More preferably, the volume of the second solvent may be in a range of 2% to 10% by volume relative to the total volume of the normal-phase eluent.

In some embodiments, a flow rate of the third eluent may depend on the volume of the third chromatographic column. For instance, if the volume of the third chromatographic column is V''', the flow rate of the third eluent eluting the third chromatographic column may be in a range from V''' to 3V''' per hour.

In order to provide a stationary phase of the third chromatographic column with an excellent density and stability, the pressure of the third chromatographic column may be maintained in a range from 3 to 300 bars. In some embodiments, the range in which the pressure of the third chromatographic column is maintained may be restricted in a subrange of 30 to 300 bar. It may also effectively prevent the collapse of the stationary phase while ensuring high separation efficiency and consistency of separation effect for long-term use.

In 650, a third $CoQ_{10}$-containing eluate from the third chromatographic column may be collected. In some embodiments, an eluate may be referred to as the eluent coming out of the chromatographic column, which may contain all or parts of elements in the loaded sample. In the process of elution, the presence of $CoQ_{10}$ in an eluate which is received from the first chromatographic column may be monitored according to a qualitative analysis method. Exemplary qualitative analysis method for monitoring the presence of $CoQ_{10}$ in the first eluate may include but not limited to the MS, NMR, IR, UV/Vis, GC, LC, HPLC, TLC, LC-MS, or the like, or a combination thereof. In some embodiments, TLC may be used to monitor the presence of $CoQ_{10}$ in the eluate which received from the first chromatographic column. The developing solvent to be used for TLC may not be particularly limited, and may only need to be selected according to the $CoQ_{10}$. The developing solvent may include hydrocarbons, fatty acid esters, nitriles, ethers, ketones, alcohols, fatty acids, or the like, or a combination thereof. In some embodiments, after every regular interval, for example, 1 minute, 2 minutes, 3 minutes, or the like, a newly eluate received from the third chromatographic column may be tested by TLC. If the eluate contains $CoQ_{10}$, the eluate obtained during the interval may be collected. The collected eluate may be designated as the third $CoQ_{10}$-containing eluate.

In 660, the third $CoQ_{10}$-containing eluate may be concentrated. In some embodiments, an evaporator may be utilized to remove the solvents (e.g., the seventh solvent and the eighth solvent) included in the third $CoQ_{10}$-containing eluate. Merely by way of example, a commercially available evaporator or the like may be used. The evaporator may include a circulating evaporator, a single-pass evaporator, a contact heat transfer evaporator, or the like, or a combination thereof. The circulating evaporator may include a vertical-tubes evaporator, a basket type evaporator, a Levin evaporator, or the like, or a combination thereof. The single-pass evaporator may include a rising film evaporator, a falling film evaporator, a scraper type evaporator, or the like, or a combination thereof. In some embodiments, when the solid content of the concentrated third $CoQ_{10}$-containing eluate reaches 10 to 20 g/L, the concentration process may be ended, and the concentrated third $CoQ_{10}$-containing eluate may be collected for the subsequent process, for example, crystallization.

In 670, the concentrated third $CoQ_{10}$-containing eluate may be crystallized to obtain pure $CoQ_{10}$. In some embodiments, an improved crystallization method may be performed for crystallizing the concentrated third $CoQ_{10}$-containing eluate, for example, vacuum crystallization with adiabatic cooling, solvent-out crystallization, ultrasound crystallization, continuous crystallization, or the like. Detailed descriptions related to the crystallization process may be found in FIG. 2 and the descriptions thereof.

The present invention is further described by the following examples which should not be construed as limiting the scope of the present invention.

EXAMPLES

Normal-Phase Chromatography and Reverse-Phase Chromatography (Example 1)

A $CoQ_{10}$-containing crude product was loaded to a chromatographic column filled with silica gel at a flow rate of 3 times volume of the silica gel per hour, and subjected to elution by a solution of n-hexane/acetone (volume ratio: 9/1) in a flow rate of 3 times volume of the silica gel per hour, and under a pressure of 300 bar to obtain a fraction containing $CoQ_{10}$. The weight of pure $CoQ_{10}$ in the loaded $CoQ_{10}$-containing crude product was 30% of the weight of the silica gel, and particle size of the silica gel was 10 μM. The fraction was concentrated to give a $CoQ_{10}$ concentrate. Then, the $CoQ_{10}$ concentrate was dissolved with acetone/alcohol (volume ratio: 9/1) solution, and the resultant was loaded to a chromatographic column filled with silica gel bonded having an octadecyl group at a flow rate of 3 times volume of the filler per hour. The chromatographic column was eluted by an acetone/alcohol (volume ratio: 3/7) solution in a flow rate of 3 times volume of the filler per hour and under a pressure of 300 bar to give a $CoQ_{10}$-containing fraction. The weight of pure $CoQ_{10}$ in the resultant was 20% of the weight of the filler, and a particle size of the filler was 10 μM. The $CoQ_{10}$-containing fraction was concentrated into a concentration of 15 g/L, and the concentrated $CoQ_{10}$-containing fraction was crystallized to obtain a purified $CoQ_{10}$ product. The purity of the purified $CoQ_{10}$ product was not less than 99.7%.

Vacuum Crystallization (Example 2)

The concentrated $CoQ_{10}$-containing fraction obtained in Example 1 was dissolved in alcohol having a volume 15 times the volume of the concentrated $CoQ_{10}$-containing fraction, the resultant was heated up to 70° C. with stirring to obtain a completely dissolved solution. The temperature of the solution was maintained at 70° C. for 30 minutes. Then, the solution was transmitted into a crystallizer (e.g., a vacuum crystallizer). Furthermore, the solution was concentrated under 22° C. and a negative pressure of 0.07 MPa to obtain a slurry. The volume of the obtained slurry was ⅓ of the volume of the solution. The slurry was transmitted to a centrifuge for centrifuging 15 minutes, the resulting wet crystals were washed with 20 liters of alcohol, and the wet crystals were centrifuged for 90 minutes to obtain $CoQ_{10}$ crystals.

Solvent-Out Crystallization (Example 3)

The concentrated $CoQ_{10}$-containing fraction obtained in Example 1 was dissolved in ethyl acetate having a volume that is the same as or substantially the same as the volume of the concentrated $CoQ_{10}$-containing fraction, and the resultant was heated up to 45° C. with stirring to obtain a dissolved solution. The temperature of the solution was maintained with 45° C. for 30 minutes. Methanol having a volume 2 times the volume of the solution was added to the solution while stirring the solution at a rate of 15 revolutions per minute. Furthermore, the solution was cooled down to 22° C. with stirring. The cooled solution was aged for 1.5 hours, and then transmitted to a centrifuge for centrifuging 15 minutes. The resulting wet crystals were washed with 20 liters alcohol, and the wet crystals were centrifuged for 90 minutes to obtain $CoQ_{10}$ crystals.

Ultrasound Crystallization (Example 4)

The concentrated $CoQ_{10}$-containing fraction obtained in Example 1 was dissolved in alcohol having a volume 8 times the volume of the concentrated $CoQ_{10}$-containing fraction, the resultant was heated up to 65° C. with stirring to obtained a completely dissolved solution. The temperature of the solution was maintained with 65° C. for 30 minutes. Then, the solution was cooled down to 45° C. The cooled solution was applied ultrasound with a power of 100 W for 10 minutes. Furthermore, the solution was continue cooled down to 22° C. with stirring. The cooled solution was aged for 1.5 hours, and then transmitted to a centrifuge for centrifuging 15 minutes, the resulting wet crystals were washed with 20 liters of alcohol, and the wet crystals were continued to be centrifuged for 90 minutes to obtain $CoQ_{10}$ crystals.

Continuous Crystallization with Adiabatic Cooling (Example 5)

The concentrated $CoQ_{10}$-containing fraction obtained in Example 1 was dissolved in alcohol having a volume 8 times the volume of the concentrated $CoQ_{10}$-containing fraction, the resultant was heated up to 65° C. with stirring to obtain a completely dissolved solution. The temperature of the solution was maintained with 65° C. for 30 minutes. Then, the solution was transmitted into a cooling crystallizer by a peristaltic pump. The solution was crystallized in the cooling crystallizer under 41° C. for 1.5 hours, the resultant was transmitted to another cooling crystallizer for crystallization under 22° C. for 2 hours to obtain a slurry. The slurry was transmitted to a centrifuge for centrifuging 15 minutes, the resulting wet crystals were washed with 20 liters alcohol, and the wet crystals were continued to be centrifuged for 90 minutes to obtain $CoQ_{10}$ crystals.

Drying (Example 6)

The $CoQ_{10}$ crystals obtained after crystallization was transferred to a sphere vacuum dryer manually. The $CoQ_{10}$ crystals were dried under a vacuum or substantially vacuum environment and a stirring condition (the revolution of the main stirrer was 50 r/min, and the revolution of the sub-stirrer was 600 r/min). $CoQ_{10}$ particles were obtained after drying at 42° C. for 8 hours.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

We claim:
1. A method for producing purified coenzyme $Q_{10}$ ($CoQ_{10}$), comprising:
   loading a $CoQ_{10}$-containing crude product into a first chromatographic column, wherein the first chromatographic column is a normal-phase chromatographic column;
   eluting the first chromatographic column with a first eluent, wherein the first eluent is a normal-phase eluent including a first solvent and a second solvent; and the second solvent is 2-10% of the first eluent by volume;
   collecting a first $CoQ_{10}$-containing eluate from the first chromatographic column to obtain a first $CoQ_{10}$-containing intermediate product;
   preparing, based on the first $CoQ_{10}$-containing intermediate product, a second $CoQ_{10}$-containing intermediate product;
   dissolving the second $CoQ_{10}$-containing intermediate product with a third solvent;
   loading the dissolved second $CoQ_{10}$-containing intermediate product into a second chromatographic column, wherein the second chromatographic column is a reverse-phase chromatographic column;
   eluting the second chromatographic column with a second eluent;
   collecting a second $CoQ_{10}$-containing eluate from the second chromatographic column; and
   concentrating the second $CoQ_{10}$-containing eluate to obtain the third $CoQ_{10}$-containing intermediate product;

wherein the second eluent is a reverse-phase eluent, the third solvent is also a reverse-phase eluent, and the second eluent including a fourth solvent and a fifth solvent, the third solvent includes at least one of ethyl acetate, butanone, dichloromethane, methyl acetate, propyl acetate, isopropyl acetate, butyl acetate, methyl propionate, ethyl propionate, butyl propionate, diethyl ether, isopropyl ether, n-propanol, isopropanol, n-butanol, or isobutanol, and at least one of methanol or acetonitrile, wherein the at least one of ethyl acetate, butanone, dichloromethane, methyl acetate, propyl acetate, isopropyl acetate, butyl acetate, methyl propionate, ethyl propionate, butyl propionate, diethyl ether, isopropyl ether, n-propanol, isopropanol, n-butanol, or isobutanol is 40-90% of the third solvent by volume; and the fourth solvent includes at least one of acetone, butanone, dichloromethane, methyl acetate, propyl acetate, isopropyl acetate, butyl acetate, methyl propionate, ethyl propionate, butyl propionate, isopropyl ether, n-propanol, isopropanol, n-butanol, or isobutanol, the fifth solvent includes at least one of alcohol, methanol, or acetonitrile, and the fourth solvent is 20-60% of the second eluent by volume; and obtaining purified $CoQ_{10}$ product by purifying the third $CoQ_{10}$-containing intermediate product through crystallization of the third $CoQ_{10}$-containing intermediate product, wherein the crystallization of the third $CoQ_{10}$-containing intermediate product includes at least one of vacuum insulation crystallization, solvent-out crystallization, ultrasound crystallization, or continuous crystallization.

2. The method of claim 1, wherein a purity of the purified $CoQ_{10}$ product is equal to or greater than 99.7%.

3. The method of claim 1, further comprising:
obtaining a mother liquor from the crystallization of the third $CoQ_{10}$-containing intermediate product; and
separating $CoQ_{10}$ from the mother liquor.

4. The method of claim 3, wherein separating $CoQ_{10}$ from the mother liquor comprises:
obtaining a fourth $CoQ_{10}$-containing intermediate product by passing the mother liquor through at least one chromatographic column; and
obtaining $CoQ_{10}$ by purifying the fourth $CoQ_{10}$-containing intermediate product through at least one crystallization of the fourth $CoQ_{10}$-containing intermediate product.

5. The method of claim 3, wherein separating $CoQ_{10}$ from the mother liquor includes:
concentrating the mother liquor to obtain a mother liquor concentrate;
dissolving the mother liquor concentrate with a sixth solvent;
loading the sixth solvent containing the mother liquor concentrate to a third chromatographic column;
eluting the third chromatographic column with a third eluent;
collecting a third $CoQ_{10}$-containing eluate from the third chromatographic column;
concentrating the third $CoQ_{10}$-containing eluate; and
crystallizing the concentrated third $CoQ_{10}$-containing eluate to obtain the purified $CoQ_{10}$.

6. The method of claim 4, wherein the at least one crystallization of the fourth $CoQ_{10}$-containing intermediate product includes at least one of vacuum insulation crystallization, solvent-out crystallization, ultrasound crystallization, or continuous crystallization.

7. The method of claim 4, wherein the at least one chromatographic column includes a normal-phase chromatographic column or a reverse-phase chromatographic column.

8. The method of claim 1, wherein the first solvent includes at least one of n-hexane, petroleum ether, n-heptane, 2-methylbutane, cyclopentane, 2-methylpentane, 2,2-dimethylbutane, 2,3-dimethylbutane, methylcyclopentane, cyclohexane, 2-methylhexane, 3-methylhexane, 2,3-dimethylpentane, 2,4-dimethylpentane, methylcyclohexane, octane, 2,2,3-trimethylpentane, isooctane, ethylcyclohexane, or 1-octene; and the second solvent includes at least one of isopropyl ether, acetone, ethyl acetate, butanone, dichloromethane, methyl acetate, propyl acetate, isopropyl acetate, butyl acetate, methyl propionate, ethyl propionate, butyl propionate, diethyl ether, methanol, ethanol, n-propanol, isopropanol, n-butanol, isobutanol, or acetonitrile.

9. The method of claim 1, wherein a pressure of the first chromatographic column or a pressure of the second chromatographic column ranges from 3 to 300 bar.

* * * * *